(12) United States Patent
Iwasaki et al.

(10) Patent No.: US 7,637,912 B2
(45) Date of Patent: Dec. 29, 2009

(54) SURGICAL INSTRUMENTS

(75) Inventors: Yoshinobu Iwasaki, Hokkaido (JP);
Kazutoshi Hida, Hokkaido (JP);
Takehiko Nakajima, Ibaraki (JP);
Masahiro Kohketsu, Saitama (JP)

(73) Assignee: Hoya Corporation, Tokyo (JP)

( * ) Notice: Subject to any disclaimer, the term of this patent is extended or adjusted under 35 U.S.C. 154(b) by 252 days.

(21) Appl. No.: 10/558,357

(22) PCT Filed: May 26, 2004

(86) PCT No.: PCT/JP2004/007581

§ 371 (c)(1),
(2), (4) Date: Dec. 4, 2006

(87) PCT Pub. No.: WO2004/105656

PCT Pub. Date: Dec. 9, 2004

(65) Prior Publication Data

US 2007/0112354 A1 May 17, 2007

(30) Foreign Application Priority Data

May 27, 2003 (JP) ............................. 2003-149725

(51) Int. Cl.
*A61F 2/00* (2006.01)
(52) U.S. Cl. ...................... 606/99; 606/86 A
(58) Field of Classification Search ............ 606/99, 606/86 A, 86 R
See application file for complete search history.

(56) References Cited

U.S. PATENT DOCUMENTS 5,645,599 A   7/1997 Samani (Continued)

FOREIGN PATENT DOCUMENTS

JP   2550758   6/1997

(Continued)

OTHER PUBLICATIONS

English Language Abstract of JP 2002-238929.

(Continued)

*Primary Examiner*—Pedro Philogene
(74) *Attorney, Agent, or Firm*—Greenblum & Bernstein, P.L.C.

(57) ABSTRACT

An object of the present invention is to provide surgical instruments which can insert a block-shaped interspinous spacer into a space between adjacent spinous processes with easier operations. The surgical instruments of the present invention are instruments for inserting the interspinous spacer having a block-like shape formed with a hollow portion into the space between the adjacent spinous processes. The surgical instruments include an insertion instrument having an inserting portion adapted to be passed through the hollow portion of the interspinous spacer, and a grasping instrument for grasping the insertion instrument, wherein the insertion instrument and the grasping instrument are adapted to be used under the condition that the insertion instrument is inserted into the hollow portion of the interspinous spacer and in such a state the grasped portion of the insertion instrument which is provided near the first end of the insertion instrument is grasped by the grasping instrument. The insertion instrument is provided with a support portion for preventing the interspinous spacer from being fallen off from the insertion instrument when the insertion instrument is inserted into the hollow portion of the interspinous spacer, at the second end thereof which is the opposite end of the first end.

20 Claims, 16 Drawing Sheets

U.S. PATENT DOCUMENTS

| | | |
|---|---|---|
| 6,451,057 B1 | 9/2002 | Chen et al. |
| 6,524,238 B2 * | 2/2003 | Velikaris et al. ............. 600/213 |
| 2002/0082695 A1 | 6/2002 | Neumann |
| 2002/0165612 A1 | 11/2002 | Gerber et al. |
| 2004/0267275 A1 * | 12/2004 | Cournoyer et al. ............ 606/99 |

FOREIGN PATENT DOCUMENTS

| | | |
|---|---|---|
| JP | 11-047175 | 2/1999 |
| JP | 2002-238929 | 8/2002 |

OTHER PUBLICATIONS

English Language Abstract of JP 11-047175.

U.S. Appl. No. 10/556,790 to Nakajima et al., filed Nov. 15, 2005.

* cited by examiner

SURGICAL INSTRUMENTS

FIELD OF THE INVENTION

The present invention relates to surgical instruments, and more particularly to surgical instruments which are used in a surgical operation for inserting an interspinous spacer into a space between adjacent spinous processes, wherein the interspinous spacer has a hollow cylindrical shape and is adapted to be used by being inserted into the space between the adjacent spinous processes.

BACKGROUND OF THE INVENTION

Spinal canal stenosis is caused by degeneration of an intervertebral disk interposed between adjacent vertebral bodies, degenerative facet joint disease, secondary deformation of a vertebral body, spinal deformation, or the like, and results in cauda equina/nerve root disorders.

One approach to treating such spinal canal stenosis includes interbody fusion in which a degenerated intervertebral disk is removed from between adjacent vertebral bodies, and then an autologous bone graft is implanted into the intervertebral space to fuse the two vertebral bodies together.

However, in a case where only bone grafting into an intervertebral space is carried out, there is a possibility that spinal instability is caused by resorption of a bone graft until bone fusion is achieved.

As a method for preventing such spinal instability, there is known a method in which an interspinous spacer is inserted into a space between adjacent spinous processes.

In the meantime, conventionally, as for surgical instruments for use in a surgical operation for inserting such an interspinous spacer into a space between adjacent spinous processes, various types of instruments have been proposed (for example, see Japanese Utility Model Registration Publication No. 2550758).

The surgical instrument disclosed in the above-mentioned prior art has a structure in which soft resin bodies are attached to inner surfaces of grasping sections, respectively, to grasp an interspinous spacer or the like directly between the soft resin bodies.

However, since such a surgical instrument grasps an interspinous spacer directly, there is a case that the interspinous spacer is damaged by an excessive grasping force or the like. Further, since the interspinous spacer is not always grasped in a predetermined portion of the instrument, it is necessary to confirm as to whether or not an interspinous spacer is inserted into a proper direction each time upon the insertion thereof, which results in a problem in that the surgical operation becomes complicated.

SUMMARY OF THE INVENTION

It is therefore an object of the present invention to provide surgical instruments which are capable of inserting an interspinous spacer into a space between adjacent spinous processes by simpler operations.

In order to achieve the above object, the present invention is directed to surgical instruments for use in a surgical operation for inserting an interspinous spacer having a block-like shape formed with a hollow portion into a space between adjacent spinous processes, the surgical instruments comprising: an insertion instrument having an inserting portion adapted to be passed through the hollow portion of the interspinous spacer, the insertion instrument having a first end and second end opposite to the first end; and a grasping instrument for grasping the insertion instrument, wherein the insertion instrument having a grasped portion to be grasped by the grasping instrument near the first end of the insertion instrument, and the insertion instrument and the grasping instrument being adapted to be used under the condition that the insertion instrument is inserted into the hollow portion of the interspinous spacer and in such a state the grasped portion of the insertion instrument is grasped by the grasping instrument.

In accordance with the present invention having the above feature, it is possible to insert the interspinous spacer into the space between the adjacent spinous processes by simpler operations.

In the present invention, it is preferred that the insertion instrument is provided with a support portion for preventing the interspinous spacer from being fallen off from the insertion instrument when the insertion instrument is inserted into the hollow portion of the interspinous spacer, at the second end thereof. This makes it possible to prevent the interspinous spacer from being off (removed) from the inserting portion.

Further, it is also preferred that the support portion has a gradually decreasing part of which cross sectional area gradually decreased toward the second end of the insertion instrument. This makes it possible to insert the interspinous spacer into the space between the adjacent spinous processes easily.

Further, it is also preferred that the support portion has a first abutment portion on which one end surface of the interspinous spacer is adapted to abut. This makes it possible to prevent the interspinous spacer from being damaged by the contact between the interspinous spacer and the support portion.

Further, it is also preferred that the grasped portion includes a first part having a cross sectional area in a plane vertical to the longitudinal direction of the insertion instrument, the cross section area of the first part being smaller than that of the insertion portion. This makes it possible for the grasped portion to grasp the insertion instrument more reliably.

Further, it is also preferred that the grasped portion includes a second part having a cross sectional area larger than that of the first part at the side of the first end from the first part. This also makes it possible to prevent the insertion instrument from being fallen off from the grasping instrument effectively.

Further, it is also preferred that the grasping instrument includes a pair of arm members each having a manipulating portion at the proximal end thereof and a grasping portion at the distal end thereof for grasping the grasped portion, in which these arm members are rotatably coupled at a pivotal point. This makes it possible to grasp the insertion instrument reliably.

Further, it is also preferred that the grasping portions are formed with grooves having a shape corresponding to the shape of the grasped portion for grasping the grasped portion. This makes it possible to grasp the insertion instrument more reliably while preventing the insertion instrument and the interspinous spacer from being damaged effectively.

Further, it is also preferred that the grasping portions include second abutment portions on which one end surface of the interspinous spacer is adapted to abut. This makes it possible to prevent the interspinous spacer from being damaged by any accidental contact more effectively.

Further, it is also preferred that the grasping instrument is bent in a direction vertical to the rotational direction of the arm members. This makes it easy to insert the interspinous spacer into the space between the adjacent spinous processes, and also makes it possible to improve manipulability of the surgical instrument in a narrow part to which the operation is to be carried out.

Further, it is also preferred that the grasping instrument is bent toward the side where the second abutment portions are provided. This also makes it easy to insert the interspinous spacer into the space between the adjacent spinous processes, and also makes it possible to improve manipulability of the surgical instrument in a narrow part to which the operation is to be carried out.

Further, it is also preferred that the first abutment portions and/or the second abutment portions have surfaces, and at least the surfaces and their vicinities of the first abutment portions and/or the second abutment portions are formed of a resin material. This makes it possible to prevent the interspinous spacer from being damaged by any accidental contact more effectively.

In this case, it is preferred that the instruments have portions adapted to abut on at least a part of the interspinous spacer, and at least a part of the portions of the instruments is formed of a resin material. This also makes it possible to prevent the interspinous spacer from being damaged by any accidental contact more effectively.

Further, it is also preferred that the resin material is mainly formed of a polyamide resin. Use of polyamide makes it possible to withstand severe condition upon sterilization and infection (such as high temperature and high pressure condition) reliably.

In the present invention, it is also preferred that the surgical instruments include a removal instrument for removing the insertion instrument from the hollow portion of the interspinous spacer. This makes it possible to remove the insertion instrument easily even in the narrow operation part.

In this case, it is preferred that the removal instrument includes a pair of arm members each having a manipulating portion at the proximal end thereof and a clamp portion at the distal end thereof for clamping the support portion of the insertion instrument which has been inserted into the hollow portion of the interspinous spacer, in which these arm members are rotatably coupled at a pivotal point. This also makes it possible to remove the insertion instrument easily even in the narrow operation part.

Further, it is also preferred that each of the clamp portions has a surface, and the surface and its vicinity of each clamp portion is formed of a resin material. This makes it possible to prevent an interspinous spacer from being damaged by any accidental contact more effectively. Further, it is also possible to hold the insertion instrument reliably.

Further, it is also preferred that the resin material is mainly formed of a polyamide resin. Use of polyamide makes it possible to withstand severe condition upon sterilization and infection (such as high temperature and high pressure condition) reliably.

Further, it is also preferred that the clamp portions form a shape corresponding to the shape of the support portion of the insertion instrument. This makes it possible to clamp the insertion instrument more reliably and to prevent effectively the insertion instrument which has been inserted into the interspinous spacer from being fallen off from the removal instrument when removing the insertion instrument from the interspinous spacer.

Furthermore, in the present invention, it is preferred that the appearance of the manipulating portion of the grasping instrument and the appearance of the manipulating portion of the removal instrument are different from each other. This makes it possible to recognize easily that they are different surgical instruments.

Furthermore, it is preferred that each of the instruments can be identified with its manipulating portion. According to the modification described above, since the kinds of the surgical instruments are identified or discriminated easily only by looking the manipulating portions thereof, it is possible to prevent mistake from being occurring in selecting the surgical instruments to be used.

These and other objects, structures and results of the present invention will be apparent more clearly when the following detailed description of the preferred embodiment is considered taken in conjunction with the appended drawings.

BEST MODE FOR CARRYING OUT THE INVENTION

Hereinbelow, surgical instruments according to the present invention will be described in detail with reference to a preferred embodiment shown in the accompanying drawings.

Figure 1:
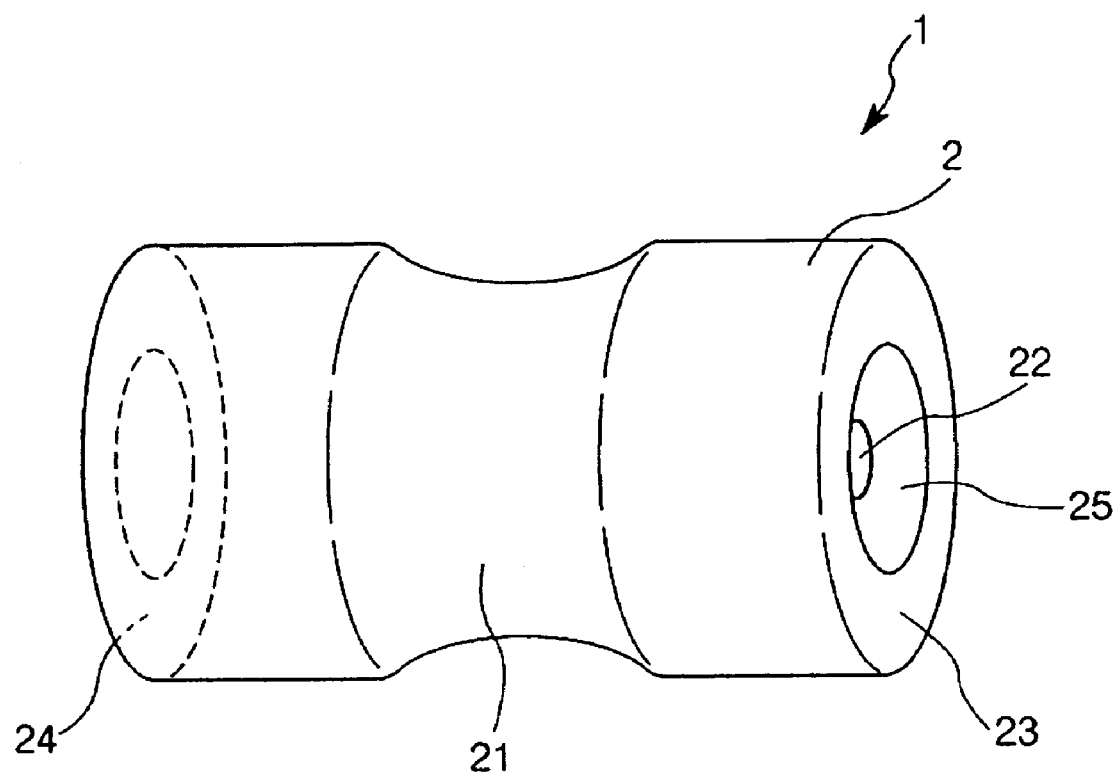
FIG. 1 is a perspective view showing a block body constituting an interspinous spacer to which surgical instruments according to the present invention are to be used.
Figure 3:
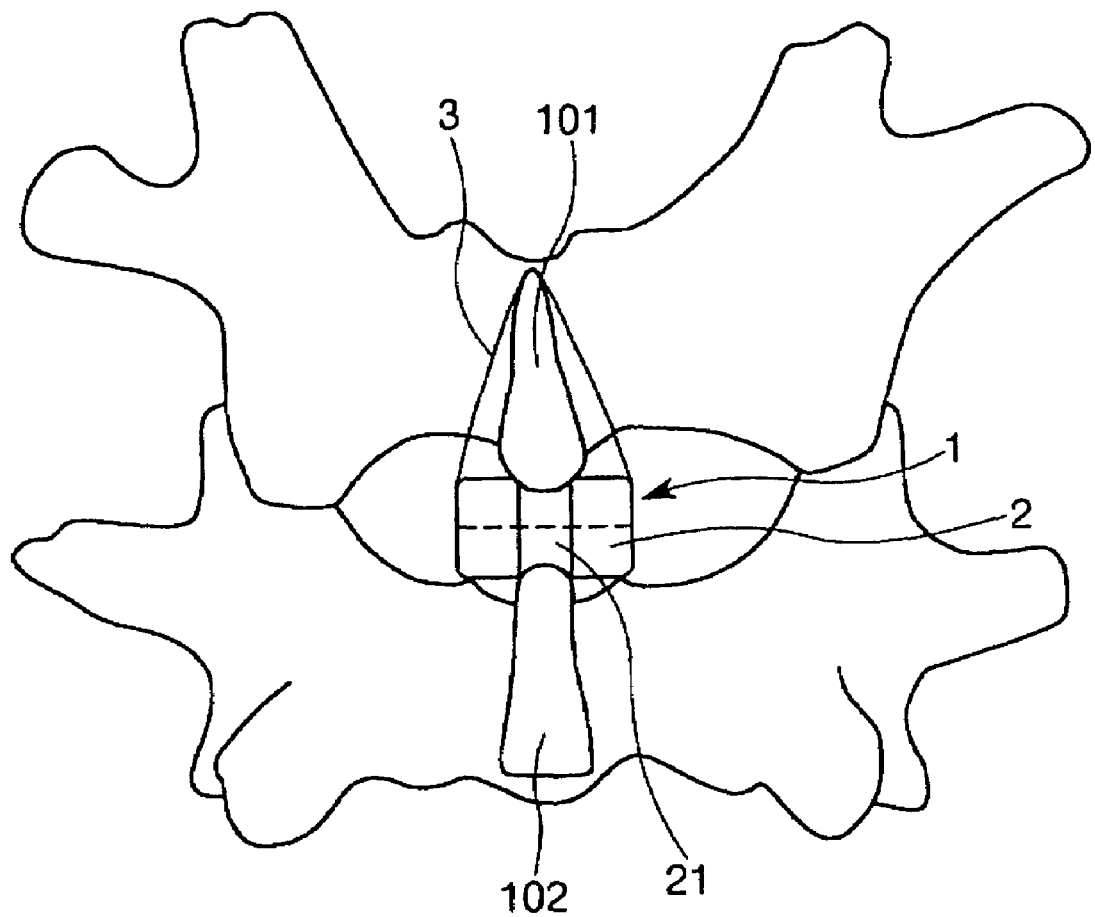
FIG. 3 is an illustration showing a state in which the interspinous spacer to which the surgical instruments according to the present invention are to be used is actually used.
Figure 4:
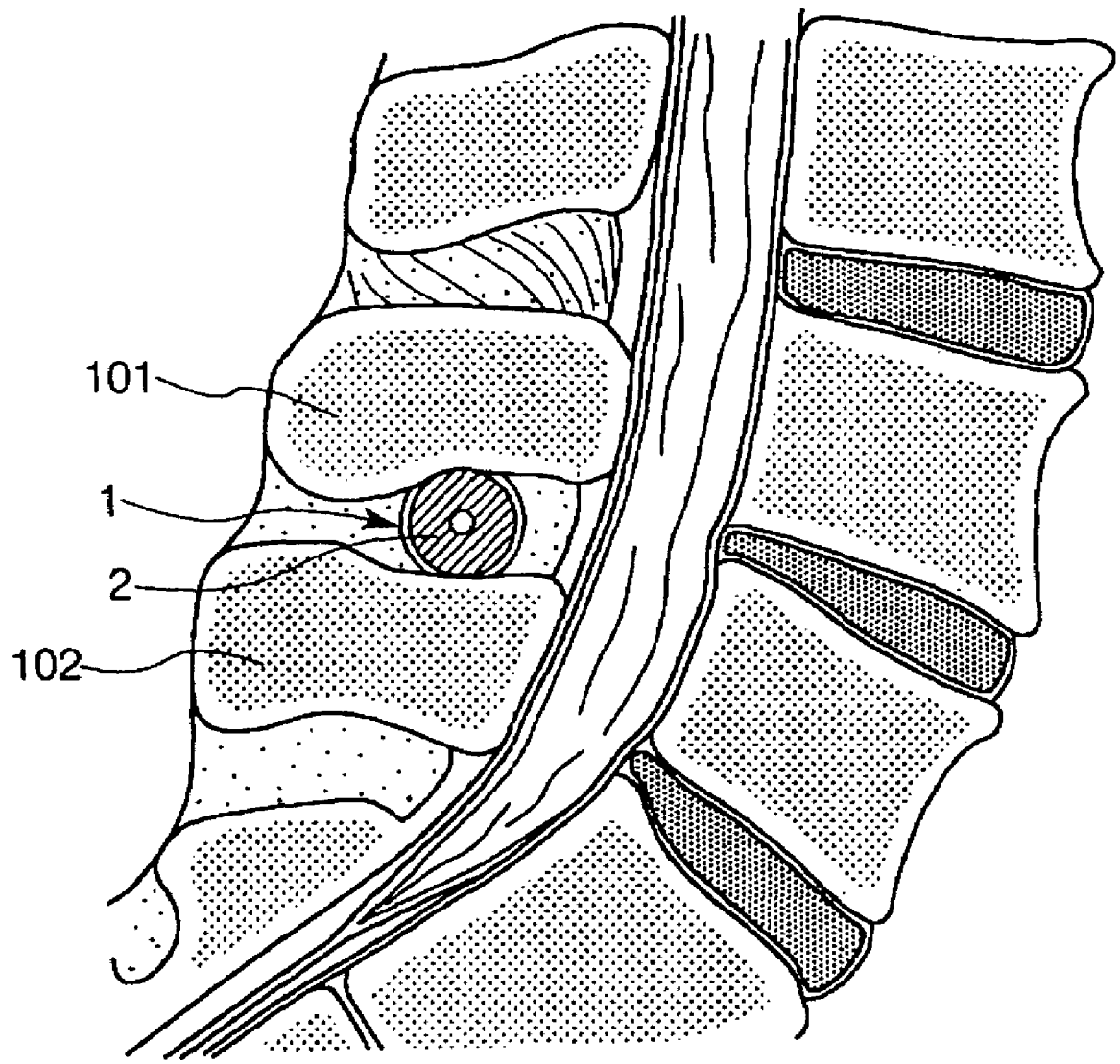
FIG. 4 is another illustration showing the state in which the interspinous spacer to which the surgical instruments according to the present invention are to be used is actually used.
Figure 5:
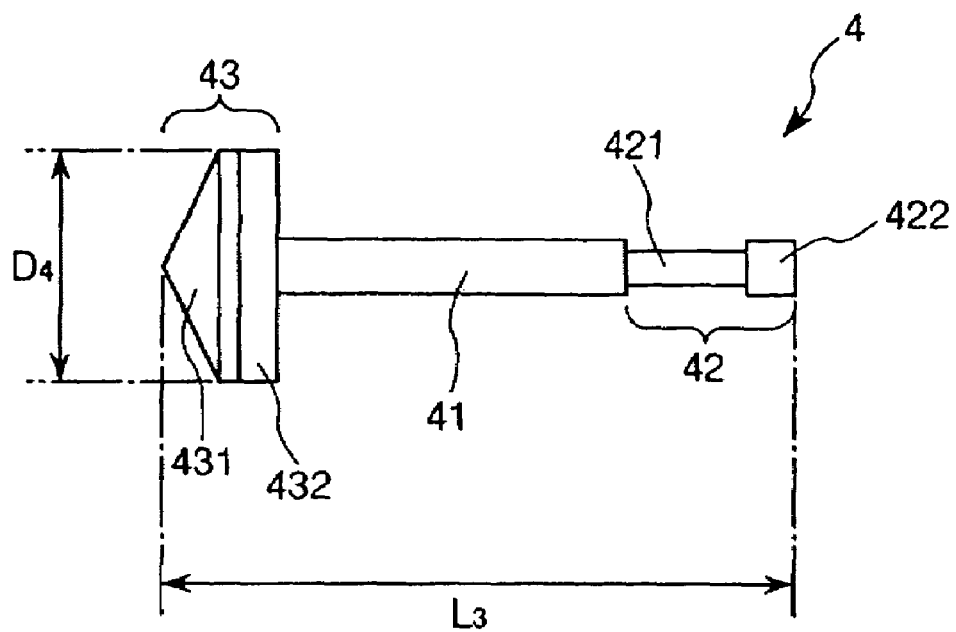
FIG. 5 is a side view of an insertion instrument which constitutes the surgical instruments according to the present invention.
Figure 6:
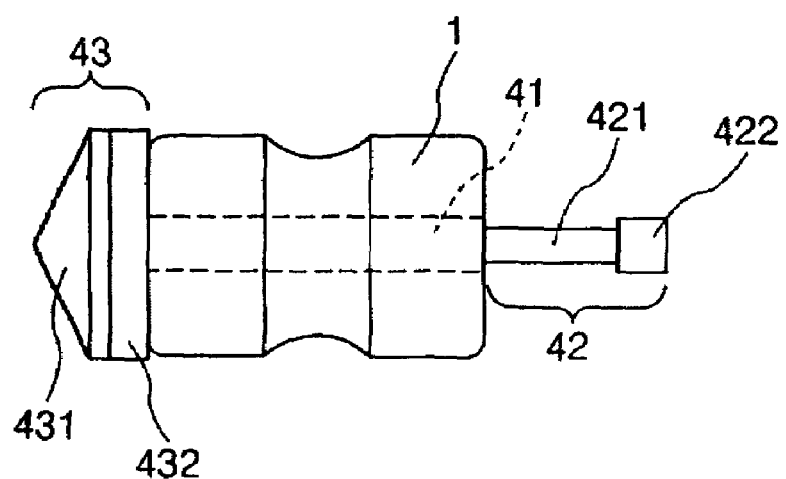
FIG. 6 is a plan view showing a state that the insertion instrument is passed through the interspinous spacer.
Figure 7:
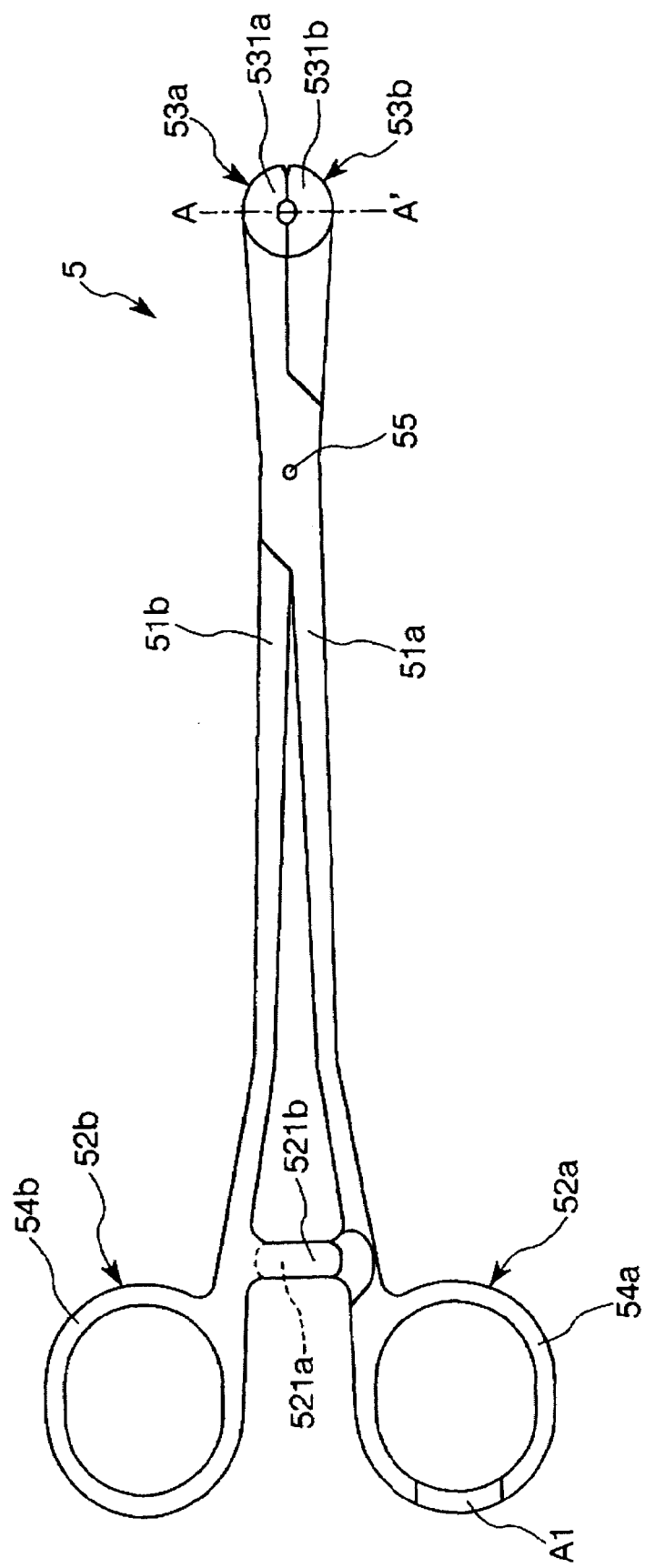
FIG. 7 is a plan view showing a state that a grasping instrument which constitutes the surgical instruments according to the present invention is closed.
Figure 8:
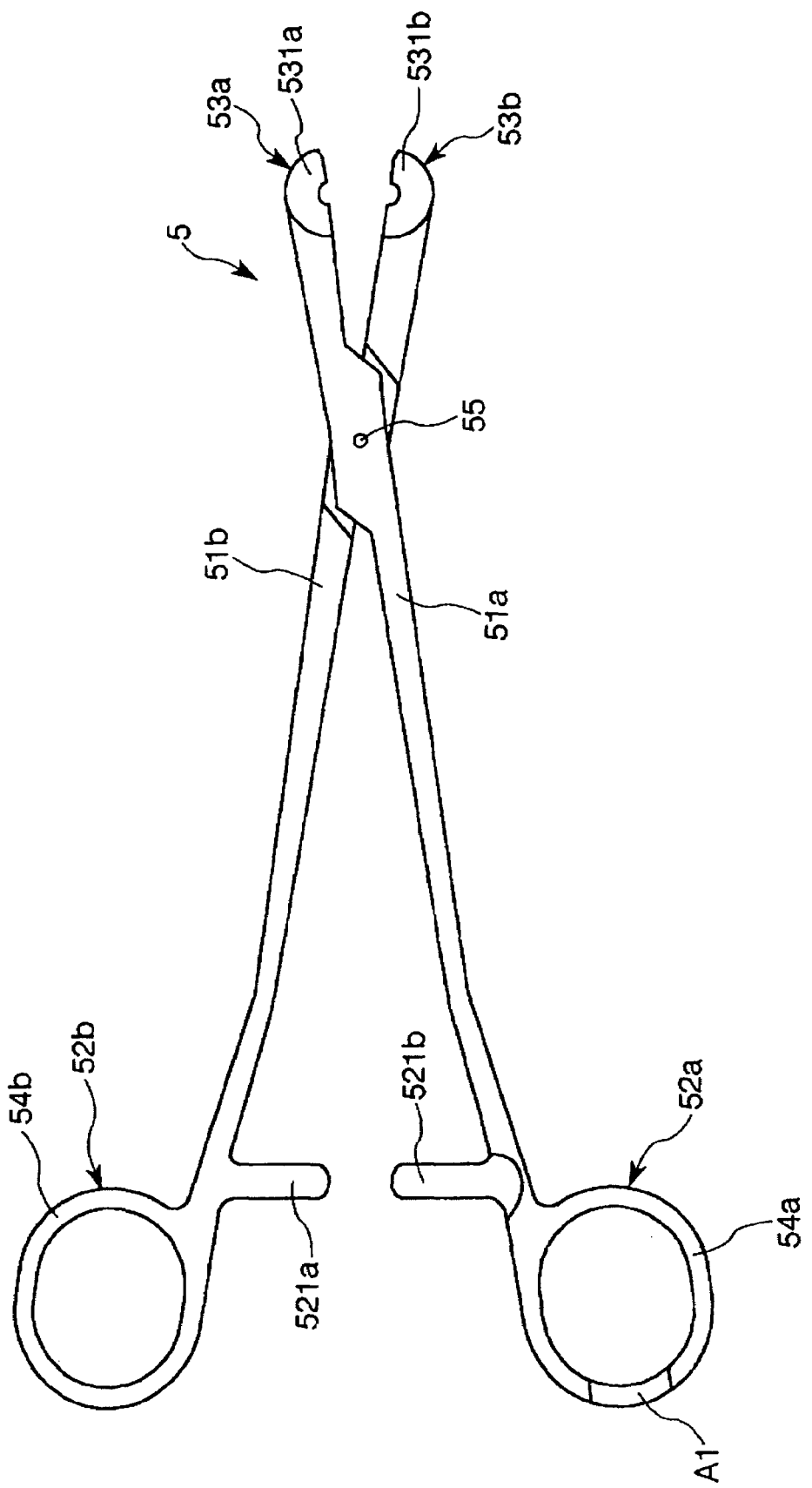
FIG. 8 is a plan view showing a state that the grasping instrument which constitutes the surgical instruments according to the present invention is opened.
Figure 9:
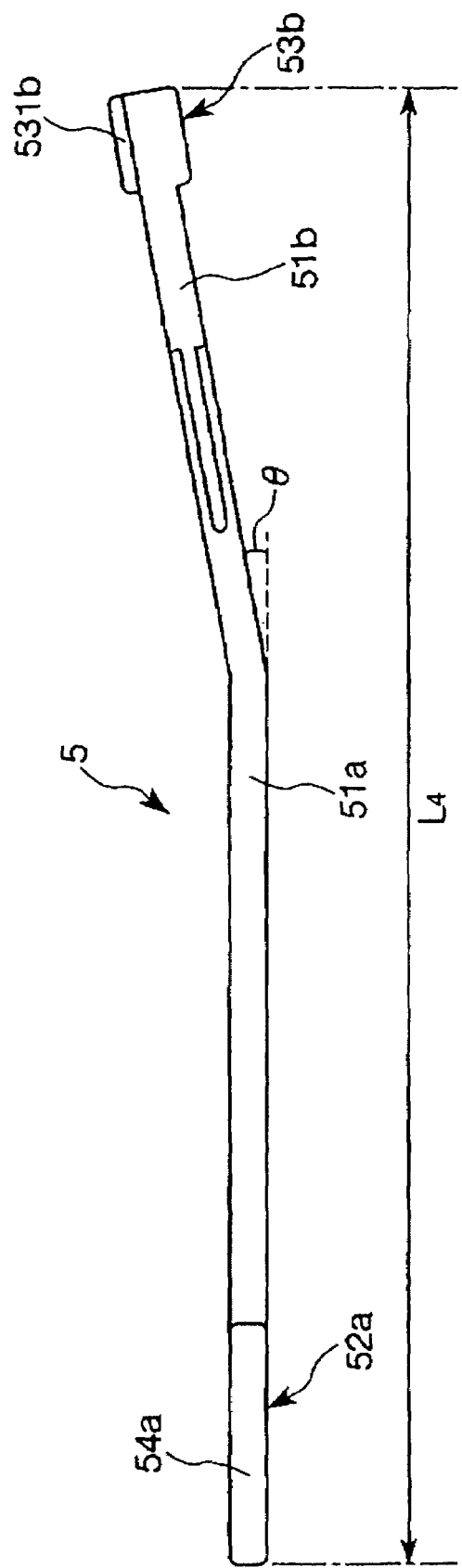
FIG. 9 is a side view of the grasping instrument which constitutes the surgical instruments according to the present invention.
Figure 10:
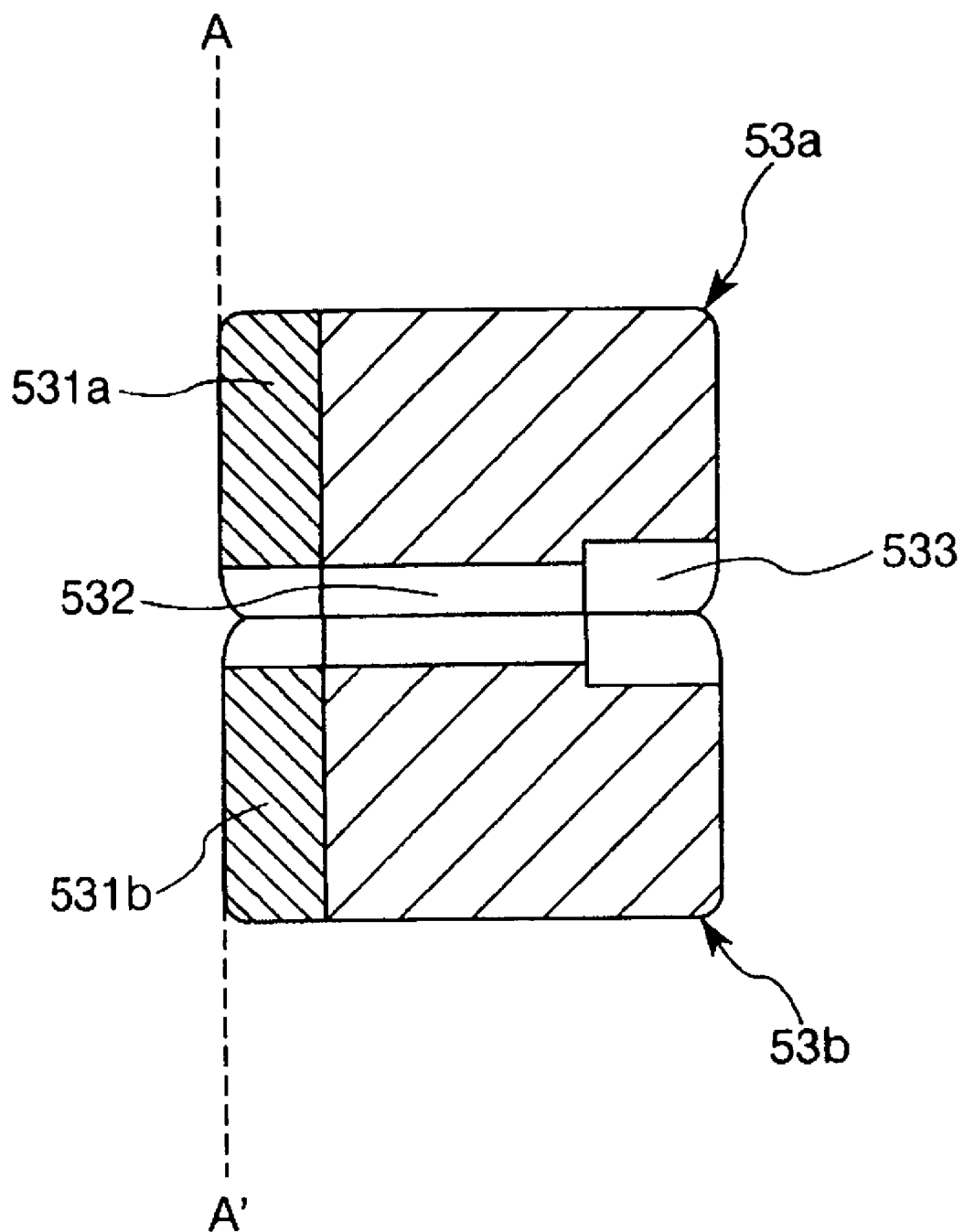
FIG. 10 is a longitudinal cross-sectional view taken along a line A-A in FIG. 7.
Figure 11:
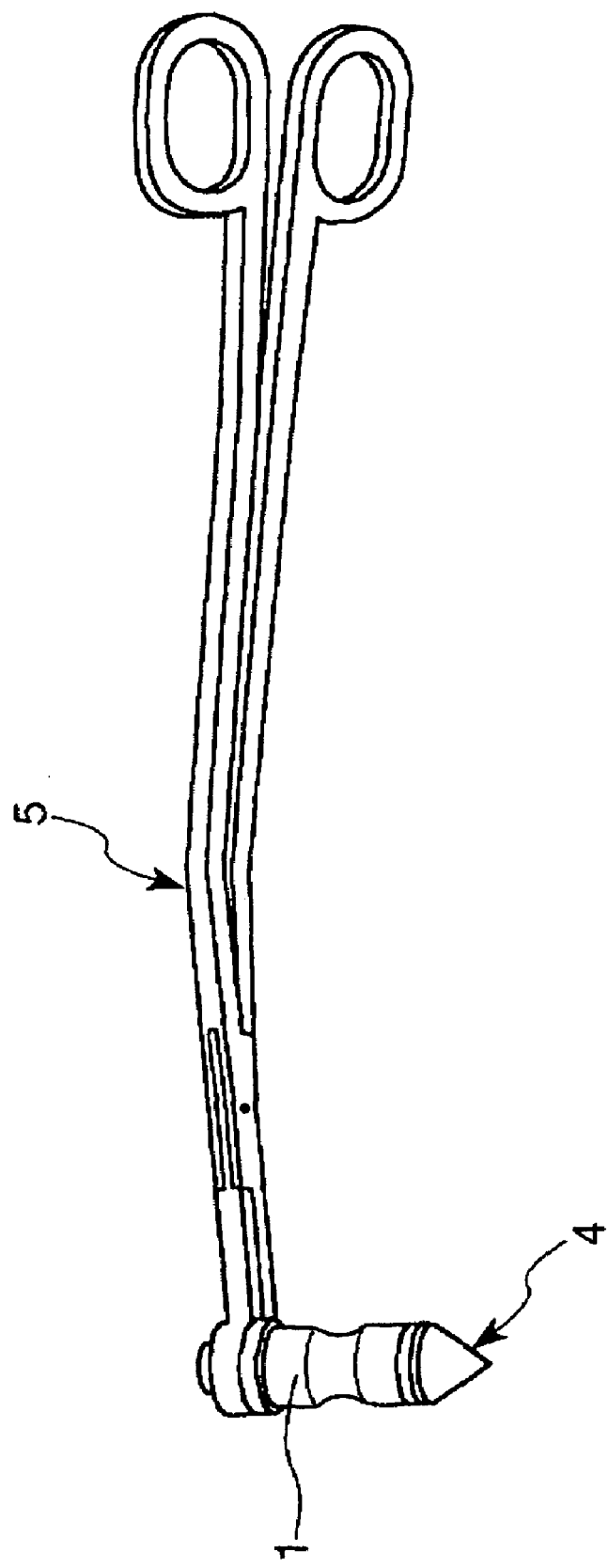
FIG. 11 is an illustration showing a state that the insertion instrument which has been inserted into the interspinous spacer is grasped with the grasping instrument.
Figure 12:
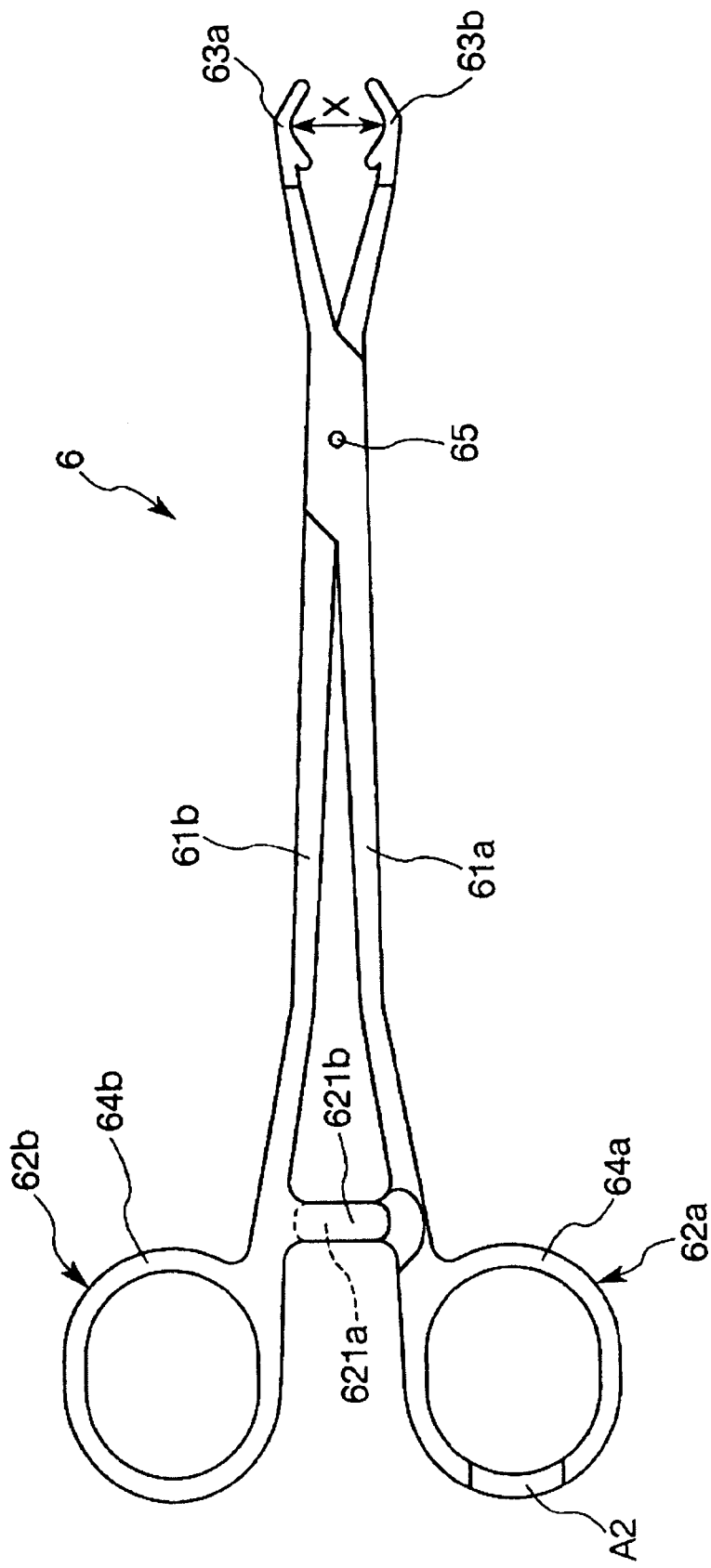
FIG. 12 is a plan view of a removal instrument which constitutes the surgical instruments according to the present invention.
Figure 13:
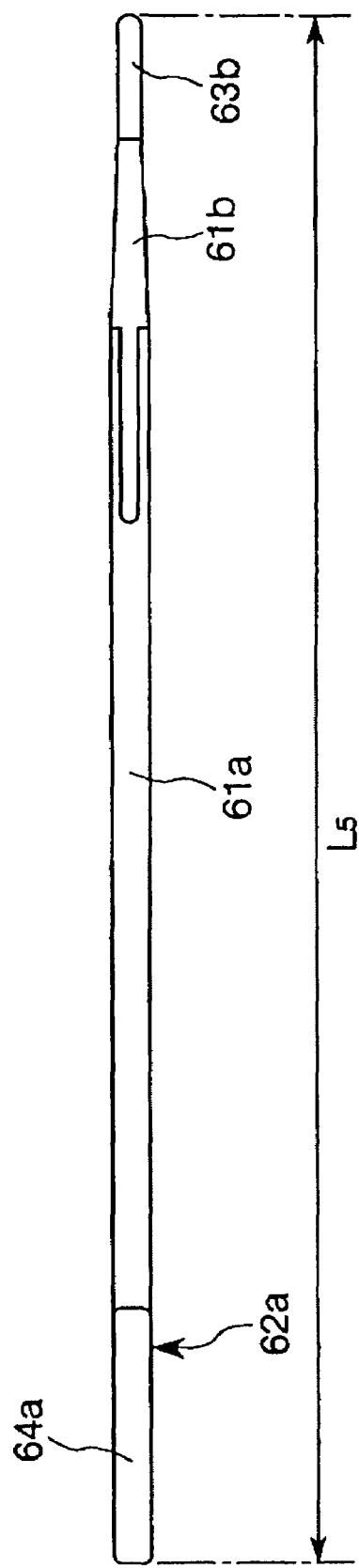
FIG. 13 is a side view of the removal instrument which constitutes the surgical instruments according to the present invention.
Figure 14:
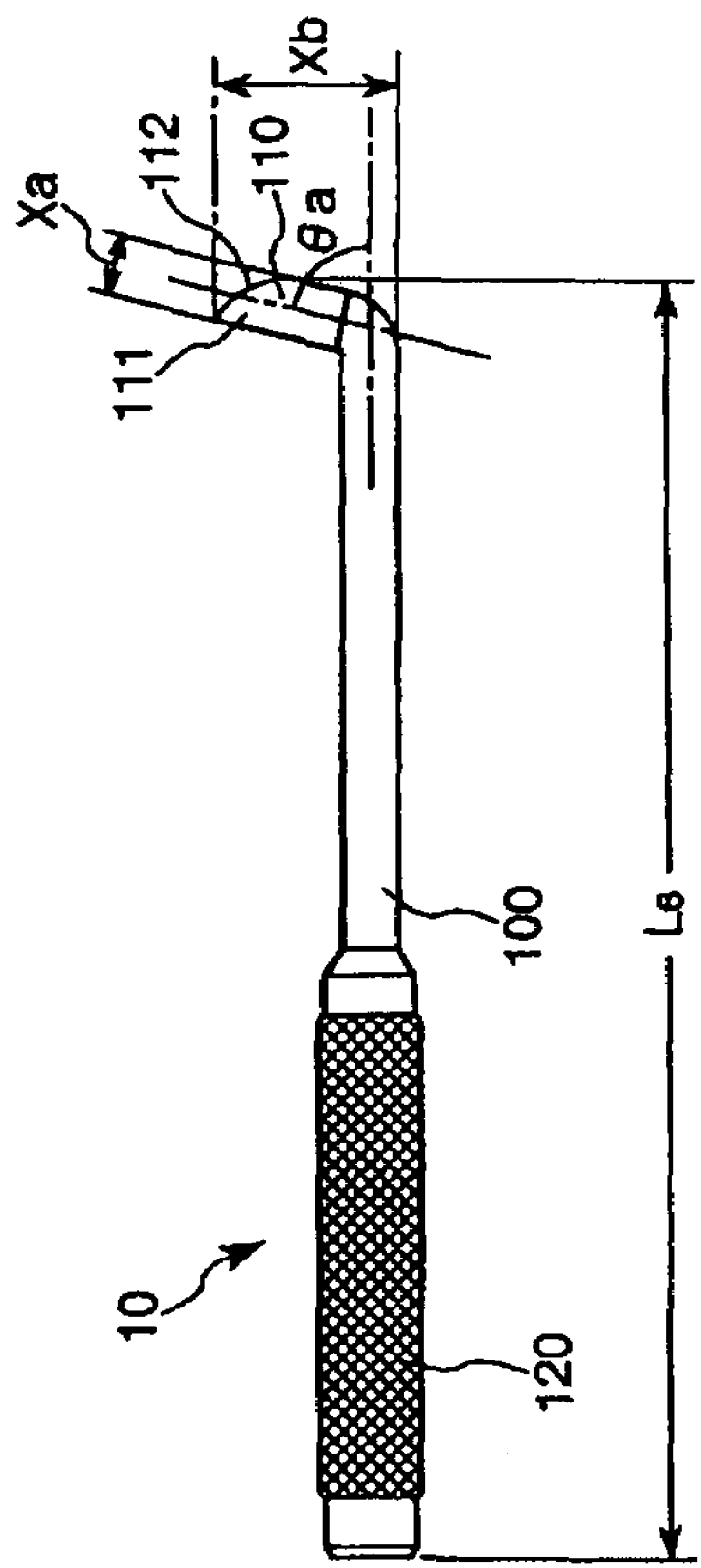
FIG. 14 is a plan view of a distracter which constitutes the surgical instruments according to the present invention.
Figure 15:
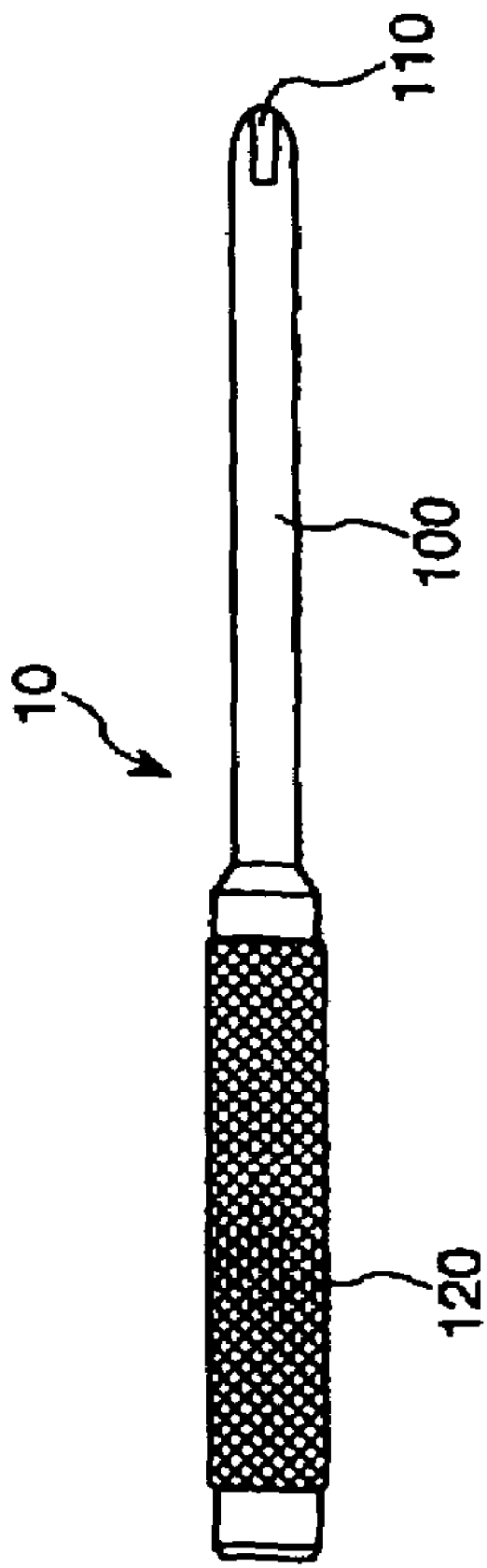
FIG. 15 is another plan view of the distracter which constitutes the surgical instruments according to the present invention.

FIG. 1 is a perspective view showing a block body constituting an interspinous spacer to which the surgical instruments according to the present invention are to be used; FIG. 2(a) is a plan view of the block body shown in FIG. 1 and FIG. 2(b) is a side view of the block body shown in FIG. 1; each of FIG. 3 and FIG. 4 is an illustration showing a state that the interspinous spacer to which the surgical instruments according to the present invention are to be used is actually used; FIG. 5 is a side view of an insertion instrument which constitutes the surgical instruments according to the present invention; FIG. 6 is a plan view showing a state that the insertion instrument is passed through the interspinous spacer; FIG. 7 is a plan view showing a state that a grasping instrument which constitutes the surgical instruments according to the present invention is closed; FIG. 8 is a plan view showing a state that the grasping instrument which constitutes the surgical instruments according to the present invention is opened; FIG. 9 is a side view of the grasping instrument; FIG. 10 is a longitudinal cross-sectional view taken along a line A-A in FIG. 7; FIG. 11 is an illustration showing a state that the insertion instrument which has been inserted into the interspinous spacer is grasped with the grasping instrument; FIG. 12 is a plan view of a removal instrument which constitutes the surgical instruments according to the present invention; FIG. 13 is a side view of the removal instrument which constitutes the surgical instruments according to the present invention; and each of FIG. 14 and FIG. 15 is a plan view of a distracter which constitutes the surgical instruments according to the present invention. In this regard, it is to be noted that in this specification the left side in FIGS. 7 to 10 and FIGS. 12 to 15 will be referred to as "proximal end" and the right side in these figures will be referred to as "distal end".

First, a description will be made with regard to an interspinous spacer to which the surgical instruments according to the present invention are to be used.

Conventionally, as an interspinous spacer for spinal canal stenosis, an interspinous spacer disclosed in U.S. Pat. No. 5,645,599 or the like has been used. Such an interspinous spacer involves a problem in that normal bone tissue is damaged when brackets are secured to adjacent spinous processes with screws to fix the spacer between the adjacent spinous processes. In addition, there is also a problem in that the interspinous spacer is complex in shape, which complicates surgical procedures.

In order to solve the problems mentioned above, the inventors of the present invention have made extensive researches, and as a result of the researches they have invented an interspinous spacer which can be reliably held between adjacent spinous processes to maintain an appropriate distance therebetween as well as allows a less invasive operation to be carried out without extensive resection of bone or soft tissue. That is, the inventors have made an invention related to such an interspinous spacer that will be described later.

As shown in FIGS. 3 and 4, an interspinous spacer 1 to which the present invention is applied is adapted to be inserted into a space between a spinous process 101 and a spinous process 102 (hereinafeter, also referred to as "interspinous space"). In a state that the interspinous spacer 1 is placed in the interspinous space (hereinafter, also referred to as "state of insertion"), an appropriate space (that is, an appropriate distance) between the spinous process 101 and the spinous process 102 is maintained.

Figure 2:
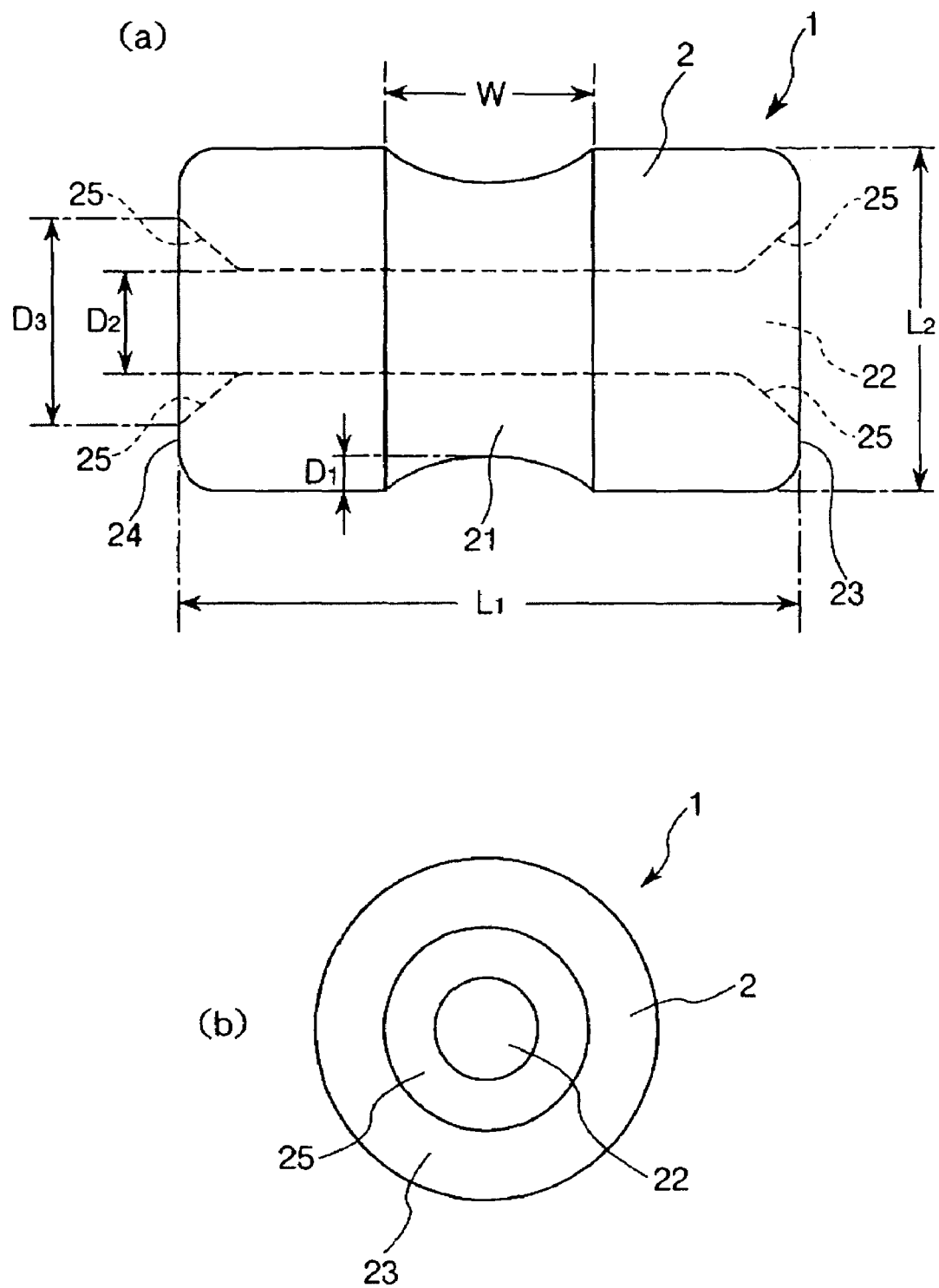
FIG. 2(a) is a plan view of the block body shown in FIG. 1
FIG. 2(b) is a side view of the block body shown in FIG. 1, wherein the block body constitutes an interspinous spacer to which the surgical instruments according to the present invention are to be used.

As shown in FIGS. 1 and 2, the interspinous spacer 1 (hereinafter, also simply referred to as "spacer 1") is composed of a block body 2 having a block-like shape.

As shown in the drawings, the block body 2 has a substantially cylindrical shape, and includes a recess 21 and a hollow portion 22. Further, the block body 2 is formed into an integral body.

As shown in FIGS. 3 and 4, the recess 21 has the function of receiving a part of each of the upper and lower spinous processes (that is, each of the adjacent spinous processes) in a state that the spacer 1 is placed in the interspinous space.

As described above, the block body 2 constituting the spacer 1 includes the recess 21 for receiving a part of each of the upper and lower spinous processes in a state that the spacer 1 is placed between the adjacent spinous processes. According to such a structure, the spacer 1 is held in an interspinous space reliably, thereby enabling an appropriate space between adjacent spinous processes to be maintained. Particularly, by using a spacer having such a structure for treatment, it is possible to carry out a less invasive operation without extensive resection of bone or soft tissue.

As shown in the drawings, the recess 21 is provided in the peripheral surface of the substantially cylindrical-shaped block body 2 in substantially the middle thereof in an axial direction. This makes it possible to hold the spacer 1 in an interspinous space reliably.

Further, the recess 21 has an arc-shaped bottom. This makes it possible to prevent more reliably surrounding tissue from being damaged either when or after the spacer 1 is inserted in an interspinous space.

The recess 21 is not particularly limited as long as it has the function of receiving a part of each of the upper and lower spinous processes in a state that the spacer 1 is placed between the adjacent spinous processes. The recess 21 may be partially provided in the block body 2 constituting the spacer 1. However, as shown in the drawings, it is preferred that the recess 21 is provided around the entire circumference of the block body 2 constituting the spacer 1. This makes it possible to hold the spacer 1 between adjacent spinous processes more reliably. In addition, such a structure is advantageous in that positioning of the spacer 1 is easily carried out when the spacer 1 is inserted into an interspinous space. Further, the recess 21 having such a structure can be easily formed when the spacer 1 is manufactured.

The depth of the recess 21 represented by "$D_1$" in FIG. 2(a) is preferably in the range of 0.5 to 10 mm, more preferably in the range of 1 to 2 mm. By setting the depth of the recess 21 to a value within the above range, it is possible to hold the spacer 1 between adjacent spinous processes more reliably. If the depth of the recess 21 is less than the above lower limit value, there is a possibility that the spacer 1 is not securely held between adjacent spinous processes. On the other hand, if the depth of the recess 21 exceeds the above upper limit value, there is a possibility that the strength of the spacer 1 itself is decreased or an appropriate space between adjacent spinous processes is not maintained.

The width of such a groove-like recess 21 represented by "W" in FIG. 2(a) is preferably in the range of 1 to 15 mm, more preferably in the range of 5 to 10 mm. By setting the width of the recess 21 to a value within the above range, it is possible to hold the spacer 1 in an interspinous space more reliably. If the width of the recess 21 is less than the above lower limit value, there is a case that it is difficult for the recess 21 to properly receive spinous processes. On the other hand, if the width of the recess 21 exceeds the above upper limit value, there is a possibility that the spacer 1 is not securely held between adjacent spinous processes.

As described above, the interspinous spacer 1 (that is, the block body 2) to which the surgical instruments according to the present embodiment are adapted to be used has a substantially cylindrical shape, and therefore surrounding tissue is not easily damaged either when or after the spacer 1 is inserted in an interspinous space.

The spacer 1 is adapted to be fixed between adjacent spinous processes, but the spacer 1 may be fixed in such a manner that it has a certain degree of freedom of movement. By allowing the spacer 1 to have a certain degree of freedom of movement, the spacer 1 can be moved in response to the movements (postures) of a human body, thereby reducing burdens on the human body.

As shown in FIGS. 1 and 2, the hollow portion 22 is provided so as to pass through the block body 2 from near the middle of a side surface 23 to near the middle of a side surface 24. That is, the hollow portion 22 is located in substantially the middle of the block body 2 so as to be in parallel with the longitudinal direction of the block body 2 (that is, in parallel with the axial direction of the cylinder).

The hollow portion 22 can be used for, for example, passing therethrough a surgical instrument for inserting an interspinous spacer 1 in a space between adjacent spinous processes. Further, the hollow portion 22 may be used for passing therethrough a fixing member 3 for fixing the interspinous spacer 1 between adjacent spinous processes with the fixing member 3. By fixing the interspinous spacer 1 in such a manner, it is possible to hold the spacer 1 in an interspinous space more reliably.

As shown in FIG. 2, the hollow portion 22 has an end portion, which slopes toward an opening, on either side thereof. Specifically, the hollow portion 22 has a gradually increasing portion 25 on either side thereof, and each of the gradually increasing portions 25 slopes toward an opening (that is, toward the end of the block body 2) so that the cross sectional area of the hollow portion 22 gradually increases in a direction perpendicular to the axial direction of the block body 2 having a substantially cylindrical shape. By providing such a gradually increasing portion 25, it is possible to, for example, prevent the fixing member 3 from coming loose or effectively prevent the fixing member 3 from being damaged due to the movement of the spacer 1 when the spacer 1 is fixed between adjacent spinous processes using the fixing member 3 which has been passed through the hollow portion 22 of the spacer 1. In addition, the gradually increasing portion 25 functions as a guide portion when the fixing member 3 is passed through the hollow portion 22.

The diameter of the hollow portion 22 represented by "$D_2$" in FIG. 2(a) is not particularly limited, but is preferably in the range of 1 to 5 mm, more preferably in the range of 2 to 4 mm. If the diameter of the hollow portion 22 is less than the above lower limit value, there is a case that it is difficult to pass the fixing member 3 through the hollow portion 22. On the other hand, if the diameter of the hollow portion 22 exceeds the above upper limit value, there is a possibility that the interspinous spacer 1 cannot have adequate strength required for an interspinous spacer.

The diameter of the gradually increasing portion 25 in the vicinity of the opening of the hollow portion represented by "$D_3$" in FIG. 2(a) is not particularly limited, but is preferably in the range of 2 to 8 mm, more preferably in the range of 4 to 6 mm. By setting the diameter of the gradually increasing portion 25 in the vicinity of each opening of the hollow portion to a value within the above range, the above-described effects become conspicuous.

The fixing member 3 to be used for fixing the interspinous spacer 1 between adjacent spinous processes is not particularly limited, but, for example, a wire-shaped fixing member can be used. Specific examples of such a wire-shaped fixing member 3 include cables made of high molecular polyethylene, sutures made of polyester, and wires made of titanium or stainless steel.

The entire length of the block body 2 having the above-described structure and represented by "$L_1$" in FIG. 2(a) is preferably in the range of 10 to 40 mm, more preferably in the range of 15 to 25 mm. If the "$L_1$" is less than the above lower limit value, there is a case that the spacer 1 is not securely held between adjacent spinous processes. On the other hand, if the "$L_1$" exceeds the above upper limit value, there is a case that it is difficult to insert the spacer 1 between adjacent spinous processes.

The diameter of the block body 2 in the vicinity of each end thereof represented by "$L_2$" in FIG. 2(a) is preferably in the range of 5 to 20 mm, more preferably in the range of 8 to 15 mm. If the "$L_2$" is less than the above lower limit value, there is a possibility that the spacer 1 cannot have adequate strength or the spacer 1 is moved off a position desired when strongly shocked. In addition, there is also a possibility that an adequate interspinous space cannot be secured so that a desired therapeutic effect is not obtained. On the other hand, if the "$L_2$" exceeds the above upper limit value, there is a case that a space between adjacent spinous processes becomes too large depending on the depth of the recess 21.

The block body 2 has rounded-corners (that is, the corners of the block body 2 are chamfered). This makes it possible to prevent more reliably surrounding tissue from being damaged when the block body 2 is inserted into an interspinous space.

The block body 2 is preferably formed using a biocompatible material. Examples of a biocompatible material include metallic materials less harmful to a living body, such as titanium, titanium alloys, stainless steel, Co—Cr based alloys, and Ni—Ti based alloys, ceramic materials, and composite materials of two or more of them.

Among these materials, titanium and titanium alloys have high strength, and are therefore advantageous in that abrasion of the block body 2 is suppressed even when stress is repeatedly applied to the block body 2. In addition, the use of titanium or titanium alloys is advantageous in that an X-ray image or the like taken after a surgical operation is not distorted.

In the case where a ceramic material is used as a main material, the block body 2 can have especially excellent biocompatibility. In addition, since a ceramic material has excellent workability, it is easy to adjust the shape and size of the block body 2 by cutting work with a lathe, a drill, or the like. It is also possible to fine-adjust the size of the block body 2 in an operation site according to the size of each of the spinous processes 101 and 102, the degree of curvature of the spine, and the like, that is, according to the disease state of a patient.

Although various ceramic materials can be used for the block body 2, alumina, zirconia, bioceramics such as calcium phosphate-based compounds are particularly preferable. Among them, calcium phosphate-based compounds are particularly preferable as a constituent material of the block body 2 because they have excellent biocompatibility.

Examples of a calcium phosphate-based compound include apatites such as hydroxyapatite, fluorapatite, and carbonate apatite, dicalcium phosphate, tricalcium phosphate, tetracalcium phosphate, and octacalcium phosphate. These calcium phosphate-based compounds can be used singly or in combination of two or more of them. Among these calcium phosphate-based compounds, one having a Ca/P ratio of 1.0 to 2.0 is preferably used.

Among such calcium phosphate-based compounds, hydroxyapatite is preferably used. Hydroxyapatite has the same composition, structure, and physical properties as the major inorganic constituent of bone, and is therefore very highly biocompatible.

Further, hydroxyapatite particles to be used as a raw material for manufacturing the block body 2 are preferably presintered at 500 to 1000° C. By presintering hydroxyapatite particles at 500 to 1000° C., it is possible to suppress activity to a certain degree, thereby suppressing nonuniform sintering caused by, for example, rapid progress of sintering. As a result, a sintered body having uniform strength can be obtained.

The porosity of the thus obtained block body 2 is preferably 50% or less, more preferably in the range of about 0 to 20%. By setting the porosity of the block body 2 to a value within the above range, it is possible to allow the block body 2 to have more appropriate strength.

It is to be noted that the block body 2 can be composed of, for example, composite materials of the above-described ceramic materials and metallic materials less harmful to a living body, such as titanium, titanium alloys, stainless steel, Co—Cr based alloys, and Ni—Ti based alloys.

The surgical instruments according to the present invention are used for inserting the interspinous spacer 1 described above into a space between adjacent spinous processes.

Hereinbelow, a description will be made with regard to the surgical instruments according to the present invention.

In the following description, an explanation will be made based on the exemplary case where the surgical instruments are used for the interspinous spacer 1 shown in FIG. 1.

The surgical instruments according to the present invention are used in a surgical operation for inserting the interspinous spacer 1 described above into a space between adjacent spinous processes, and include an insertion instrument 4 and a grasping instrument 5.

As shown in FIGS. 5 and 6, the insertion instrument 4 includes an inserting portion 41 to be passed through the interspinous spacer 1, a grasped portion (that is, a portion to be grasped) 42 provided on the side of one end part (first end part) of the inserting portion 41, and a support portion 43 provided on the side of the other end part (second end part).

As shown in FIG. 6, the inserting portion 41 is adapted to be inserted into the hollow portion 22, and has the function of a guide portion for inserting the interspinous spacer 1 in a proper direction when the interspinous spacer 1 is inserted into a space between adjacent spinous processes.

The inserting portion 41 has a shape corresponding to the hollow portion 22 of the interspinous spacer 1. Namely, in the structure shown in the drawings, the inserting portion 41 is formed into a shape of which cross section (that is, a cross section along a plane which is vertical to the longitudinal direction of the insertion instrument 4) is substantially circular.

The diameter of the inserting portion 41 in its cross section is not limited to a specific value, but it is preferred that the diameter of the inserting portion 41 is substantially the same as that of the hollow portion 22 of the interspinous spacer 1. This makes it possible to insert an interspinous spacer 1 in to a space between adjacent spinous processes more reliably in a proper direction.

Practically, the diameter of the inserting portion 41 in its cross section is preferably in the range of 1 to 5 mm, and more preferably in the range of 2 to 4 mm. If the diameter of the inserting portion 41 in its cross section is less than the lower limit value, there is a case that the insertion instrument 4 can not have sufficient strength as a whole, and there is also a case that an interspinous spacer 1 can not be properly held by the insertion instrument 4 so that it can not be inserted into a space between adjacent spinous processes in a proper direction. On the other hand, if the diameter of the inserting portion 41 in its cross section exceeds the above upper limit value, there is a case that it is difficult to insert the inserting portion 41 into the hollow portion 22 of the interspinous spacer 1. In this regard, it is to be noted that the diameter of the inserting portion 41 may be constant or varied in its longitudinal direction.

The entire length of the inserting portion 41 in the longitudinal direction of the insertion instrument 4 is not particularly limited to a specific value, but it is preferred that the entire length of the inserting portion 41 is substantially the same as the entire length of the interspinous spacer 1 represented by "$L_1$" in FIG. 2(a). This makes it possible to insert an interspinous spacer 1 into a space between adjacent spinous processes more reliably in a proper direction. Practically, the entire length of the inserting portion 41 is preferably in the range of 10 to 40 mm, and more preferably in the range of 15 to 25 mm.

In the structure shown in the drawing, the grasped portion 42 is provided on the side of the first end of the insertion instrument 4 so as to be continued from the inserting portion 41, and the grasped portion 41 is a portion to be grasped by the grasping instrument 5 which will be described later.

The grasped portion 42 has a first part 421 in which a cross sectional area of the grasped portion 42 (that is, the cross section in a plane which is vertical to the longitudinal direction of the insertion instrument 4) is smaller than the cross sectional area of the inserting portion 41. This makes it possible for the grasping instrument 5 to grasp the insertion instrument 4 more reliably.

Further, the grasped portion 42 also has a second part 422 having a cross sectional area larger than that of the first part 421 at the side of the first end so as to be continued from the first part 421.

Since the grasped portion 42 has the first part 421 and the second part 422 described above, it is possible to effectively prevent the insertion instrument 4 from being fallen off from the grasping instrument 5.

The diameter of the first part 421 in its cross section is preferably in the range of 1 to 5 mm, and more preferably in the range of 2 to 4 mm. If the diameter of the first part 421 is less than the above lower limit value, there is a case that it is not possible to obtain sufficient strength required for the grasped portion 42. On the other hand, if the diameter of the first part 421 in its cross section exceeds the above upper limit value, there is a case that the effect that prevents the insertion instrument from being fallen off from the grasping instrument 5 can not be sufficiently exhibited.

The diameter of the second part 422 in its cross section is not particularly limited to a specific value, but it is preferred that the diameter of the second part 422 is substantially the same as that of the inserting portion 41 described above. This makes it possible to prevent the insertion instrument 4 from being fallen off from the grasped instrument 5 more effectively. Further, this makes it easy to remove the insertion instrument 4 from the hollow portion 22 of the interspinous spacer 1. The diameter of the second part 422 in its cross section is preferably in the range of 1 to 5 mm, and more preferably in the range of 2 to 4 mm.

The support portion 43 is provided in the vicinity of the second end of the insertion instrument 4 which is opposite to the first end thereof. Namely, the support portion 43 is provided on the side of the second end with respect to the inserting portion 41. The support portion 43 has the function of preventing the interspinous spacer 1 from being fallen off (removed) from the inserting portion 41 when the inserting portion 41 is inserted into the interspinous spacer 1.

The support portion 43 has a gradually decreasing part 431 in which its cross sectional area (cross section in a plane which is vertical to the longitudinal direction of the insertion instrument 4) is gradually decreased. This makes it possible to insert an interspinous spacer 1 into a space between adjacent spinous processes more easily.

The maximum diameter of the support portion 43 which is represented by "$D_4$" in FIG. 5 is not particularly limited to a specific value, but preferably in the range of 5 to 20 mm, and more preferably in the range of 8 to 15 mm. This makes it possible to prevent the interspinous spacer 1 from being fallen off from the inserting portion 41 effectively, and this also makes it possible to insert the interspinous spacer 1 into a space between adjacent spinous processes more easily.

The support portion 43 also has a first abutment part 432 against which one end surface of the interspinous spacer 1 abuts.

In this embodiment, the first abutment part 432 is formed of a resin material. This makes it possible to prevent the interspinous spacer 1 from being damaged by any accidental contact.

Examples of such a resin material include polyvinylchloride resin, polyurethane resin, polyester resin, polyolefin resin, polyamide resin, polystyrene resin, silicone rubber, vinyl chloride, high density polyethylene and the like. Among these materials, polyamide is particularly preferable. Use of polyamide makes it possible to withstand severe condition upon sterilization and infection (such as high temperature and high pressure condition) reliably.

The entire length of the above described insertion instrument which is represented by "$L_3$" in FIG. 5 is not particularly limited to a specific value, but preferably in the range of 15 to 50 mm, and more preferably in the range of 25 to 40 mm. If the entire length $L_3$ of the insertion instrument 4 is less than the lower limit value, there is a case that it is difficult to grasp an interspinous spacer 1 with the grasping instrument described later depending on the entire length of the interspinous spacer 1. On the other hand, if the entire length $L_3$ Of the insertion instrument 4 exceeds the above upper limit value, there is a case that it is difficult to insert an interspinous spacer 1 to which the insertion instrument 4 has been already inserted into an space between adjacent spinous processes.

As shown in FIG. 7 to FIG. 9, the grasping instrument 5 is a device comprised of a pair of elongated arm members (rod-shaped members) 51a, 51b and they are coupled together at a pivot point (pin) 55 so that the arm members are rotatable with respect to each other. The arm member 51a and the arm member 51b have a substantially symmetrical shape excepting the portions thereof in the vicinity of the pivotal point 55.

The arm member 51a has a manipulating portion (grasping and manipulating portion) 52a at the side of the proximal end thereof and a grasping portion 53a at the side of the distal end thereof. Similarly, the arm member 51b has a manipulating portion (grasping and manipulating portion) 52b at the side of the proximal end thereof and a grasping portion 53b at the side of the distal end thereof.

The arm members 51a and 51b are operated so that the grasping portions 53a, 53b are closed when the manipulating portions 52a, 52b are closed (see FIG. 7), while the grasping portions 53a, 53b are opened when the manipulating portions 52a, 52b are opened (see FIG. 8).

The manipulating portions 52a, 52b are portions for operating the grasping instrument 5 with a hand of an operator, and they are respectively formed from ringhandles 54a, 54b to which fingers of the operator are to be inserted to manipulate the instrument. In this regard, it is to be noted that the manipulating portions 52a, 52b may be formed into various shapes so long as the arm members 51a, 51b can rotatably manipulated. For example, each of the manipulating portions 52a, 52b may be formed into a C-shaped configuration (like hook) or an L-shaped configuration.

Further, the manipulating portions 52a, 52b are respectively provided with locking parts 521 so as to be able to keep a state that the insertion instrument 4 is being grasped. This makes it possible to effectively prevent the insertion instrument 4 which has been inserted into the interspinous spacer 1 from being fallen off due to an accident that the grasping instrument 5 is unintentionally opened during the surgical operation.

The grasping portions 53a, 53b are portions for grasping the grasped part 42 of the insertion instrument 4 which has been inserted into the interspinous spacer 1, and they are respectively formed with second abutment parts 531a, 531b on the sides which abut against the interspinous spacer 1.

As shown in FIGS. 7 and 10, each of the grasping portions 53a, 53b has a substantially semi-circular column shape, and the grasping portions 53a, 53b form a substantially circular column shape in a state that they are joined together, that is in a state that the grasping instrument 5 is closed.

Further, the grasping portions 53a, 53b are formed with grooves, respectively, which form a bore along the axis of the column shape when the grasping portions 53a, 53b are joined together, that is in a state that the grasping instrument 5 is closed. The shape of each of the grooves is designed so as to provide a bore having a shape corresponding to the grasped part 42 in a state that the grasping portions 53a, 53b are joined together. Namely, as shown in FIG. 10, when the grasping portions 53a, 53b are closed, the bore is created by the grooves. This makes it possible to grasp the insertion instrument 4 more reliably while preventing the insertion instrument 4 and the interspinous spacer 1 from being damaged effectively.

In the structure shown in the drawings, the bore includes a small diameter portion 532 having a relatively small diameter and a large diameter portion 533 having a relatively large diameter, and the small diameter portion 532 and the large diameter portion 533 have shapes corresponding to the first part 421 and the second part 422 of the grasped portion 42, respectively. Namely, the small diameter portion 532 grasps the first part 421 and the large diameter portion 533 grasps the second part 422. According to this structure, it is possible to prevent the insertion instrument 4 from being fallen off from the grasping instrument 5 reliably while preventing the insertion instrument 4 and the interspinous spacer 1 from being damaged effectively.

The grasping instrument 5 is slightly bent in a direction vertical to the rotational direction of the arm members 51a, 51b. In particular, as shown in the drawing, it is preferred that as shown in the drawing the grasping instrument 5 is bent toward the side on which the second abutment portions 531a, 531b are provided, and it is also preferred that the grasping instrument 5 is bent at a substantially middle thereof. This makes it easy to insert an interspinous spacer 1 into a space between adjacent spinous processes, and also makes it possible to improve manipulability of the surgical instrument in a narrow part to which the operation is to be carried out.

The bent angle described above (that is, the angle shown by θ in FIG. 9) is not particularly limited to a specific value, but in order to exhibit the effects described above effectively, the bent angle is preferably in the range of 30 to 150° and more preferably in the range of 60 to 120°.

Further, it is preferred that at least the surface and its vicinity of each of the second abutment portions 531a, 531b is formed of a resin material. This makes it possible to prevent an interspinous spacer 1 from being damaged by any accidental contact more effectively.

Examples of such a resin material includes polyvinylchloride resin, polyurethane resin, polyester resin, polyolefin resin, polyamide resin, polystyrene resin, silicone rubber, vinylchloride, high density polyethylene and the like. Among these materials, polyamide is particularly preferable. Use of polyamide makes it possible to withstand severe condition upon sterilization and infection (such as high temperature and high pressure condition) reliably.

The entire length of the grasping instrument 5 when view from the top thereof (that is, the length represented by "$L_4$" in FIG. 9) is not particularly limited to a specific value, but preferably in the range of 100 to 250 mm, and more preferably in the range of 180 to 220 mm. This makes it possible to improve manipulability of the grasping instrument 5.

The surgical instruments of this embodiment further include a removal instrument 6.

Hereinbelow, a description will be made with regard to the removal instrument 6.

The removal instrument 6 is used to remove the insertion instrument 4 after the interspinous spacer 1 with the insertion instrument 4 has been inserted into a space between adjacent spinous processes.

As shown in FIGS. 12 and 13, the removal instrument 6 is a device comprised of a pair of elongated arm members (rod members) 61a, 61b and they are coupled together at a pivot point (pin) 65 so that the arm members are rotatable with respect to each other. The arm member 61a and the arm member 61b have a substantially symmetrical shape excepting the portions thereof in the vicinity of the pivotal point 65.

The arm member 61a has a manipulating portion (grasping and manipulating portion) 62a at the side of the proximal end thereof and a clamp portion 63a at the side of the distal end thereof. Similarly, the arm member 61b has a manipulating portion (grasping and manipulating portion) 62b at the side of the proximal end thereof and a clamp portion 63b at the side of the distal end thereof.

The arm members 61a and 61b are operated so that the clamp portions 63a, 63b are closed when the manipulating portions 62a, 62b are closed, while the clamp portions 63a, 63b are opened when the manipulating portions 62a, 62b are opened.

The manipulating portions 62a, 62b are portions for operating the removal instrument 6 with a hand of an operator, and they are respectively formed from ringhandles 64a, 64b to which fingers of the operator are to be inserted to manipulate the instrument. In this regard, it is to be noted that the manipulating portions 62a, 62b may be formed into various shapes so long as the arm members 61a, 61b can rotatably manipulated. For example, each of the manipulating portions 62a, 62b may be formed into a C-shaped configuration (like hook) or an L-shaped configuration.

Further, the manipulating portions 62a, 62b are respectively provided with locking parts 621a, 621b so as to be able to keep a state that the insertion instrument 4 is being clamped. This makes it possible to prevent effectively the insertion instrument 4 which has been inserted into the interspinous spacer 1 from being fallen off due to an accident that the removal instrument 6 is unintentionally opened when removing the insertion instrument 4 from the interspinous spacer 1.

As shown in FIG. 12, the clamp portions 63a, 63b have shapes corresponding to the support portion 43 of the insertion instrument 4, and the distance of the spacing between the clamp portion 63a and the clamp portion 63b in a state that the removal instrument 6 is closed (that is, the distance represented by "X" in the figure) is slightly smaller than the maximum diameter of the support portion 43 described above. This makes it possible to reliably clamp the insertion instrument 4, and thus it is possible to prevent effectively the insertion instrument 4 from being fallen off from the removal instrument 6 when removing the removal instrument 4 from the interspinous spacer 1.

It is preferred that at least the surface and its vicinity of each of the clamp portions 63a, 63b is formed of a resin material. This makes it possible to prevent an interspinous spacer 1 from being damaged by any accidental contact more effectively. Further, it is also possible to hold the insertion instrument 4 reliably.

Examples of such a resin material includes polyvinylchloride resin, polyurethane resin, polyester resin, polyolefin resin, polyamide resin, polystyrene resin, silicone rubber, vinylchloride, high density polyethylene and the like. Among these materials, polyamide is particularly preferable. Use of polyamide makes it possible to withstand severe condition upon sterilization and infection (such as high temperature and high pressure condition) reliably.

The entire length of the removal instrument 6 when viewed from the top thereof (that is, the length represented by "$L_5$" in FIG. 13) is not particularly limited to a specific value, but preferably in the range of 100 to 250 mm, and more preferably in the range of 180 to 220 mm. This makes it possible to improve manipulability of the removal instrument 6.

Furthermore, the surgical instruments of the present invention also include a distracter 10 in addition to the insertion instrument 4, the grasping instrument 5 and the removal instrument 6 described above.

The distracter 10 is used, before inserting an interspinous spacer 1 into a space between adjacent spinous processes, for widening interspinal ligaments.

As shown in FIG. 14 and FIG. 15, the distracter 10 comprises a rod-shaped main body 100, an inserting portion provided on the distal end of the main body 100 and adapted to be inserted into interspinal ligaments, a grip portion 120 provided on the proximal end of the main body for holding the distracter 100.

As shown in the figures, the inserting portion 110 is provided so as to protrude in a direction roughly perpendicular to the longitudinal direction of the main body 100.

In this connection, it is to be noted that the angle between the longitudinal direction of the main body 100 and the protruding direction of the insertion part 110 (that is, the angle represented by "θ" in the figures) is preferably in the range of 50 to 110°, and more preferably in the range of 60 to 100°. This makes it possible to improve operability of the distracter 10.

The inserting portion 110 is formed into a thin plate-like shape of which thickness is thinner than the thickness (diameter) of the main body 100. By forming the inserting portion 110 to such a shape, it is possible to insert the inserting portion 110 into interspinal ligaments relatively easily. Further, it is also possible to widen the interspinal ligaments by rotating the inserting portion 110 after it has been inserted thereinto.

Practically, it is preferred that the average thickness of the inserting portion 110 is in the range of 2 to 8 mm. This makes it possible to insert the inserting portion into interspinal ligaments easily.

Further, it is also preferred that the width of the inserting portion 110 which is represented by "$X_a$" in FIG. 14 is in the range of 8 to 15 mm. This makes it possible to widen interspinal ligaments by rotating the inserting portion 110 after it has been inserted thereinto.

Further, the inserting portion 110 has a gradually decreasing part 111 of which cross sectional area is gradually decreased from the base of the inserting portion 110 coupled to the main body 100 toward the protruding direction of the inserting portion 110, that is, toward the tip part of the inserting portion 110. By forming such a gradually decreasing part 111, it is possible to insert the distracter 10 into interspinal ligaments relatively easily.

Furthermore, as shown in FIG. 14, the inserting portion 110 also has a curved part 112 near the tip thereof. This makes it possible to prevent surrounding tissues from being damaged more reliably when inserting the inserting portion 110 into interspinal ligaments.

Moreover, on the outer peripheral surface of the grip portion 120, there are formed fine irregularities. This make it possible to improve operability of the distracter 10 further.

The entire length of the distracter 10 when viewed from the top thereof (that is, the length represented by "$L_6$" in FIG. 14) is not limited to a specific value, but preferably in the range of 150 to 300 mm, and more preferably in the range of 20 to 250 mm. This also makes it possible to improve operability of the distracter 10 further.

Further, the width of the vicinity of the tip of the distracter 10 which is represented by "$X_b$" in FIG. 14 is preferably in the range of 20 to 45 mm. This makes it possible to insert the inserting portion 110 into interspinal ligaments more reliably.

In the foregoing, the present invention was described based on the preferred embodiment. However, in the present invention, it is preferred that the manipulating portions 52a and/or 52b of the grasping instrument 5 and the manipulating portions 62a and/or 62b of the removal instrument 6 have different outer appearances, respectively. This makes it possible to recognize easily that they are different surgical instruments.

In this case, it is possible to change the outer appearances of the manipulating portions by a method in which different shapes, sizes, materials, hand feelings, colors, or the like are given to the manipulating portions of the respective instruments, and/or a method in which different makers such as letters (numerals), symbols, figures, or the like are applied to the manipulating portions of the respective instruments.

For example, in the structures shown in the drawings, a part of the manipulating portion 52a of the grasping instrument 5 shown by A1 and a part of the manipulating portion 62a of the removal instrument 6 shown by A1 may be configured so that these parts A1 and A2 have different colors or different numerals, respectively.

According to the modification described above, since the kinds of the surgical instruments are identified or discriminated easily only by looking the manipulating portions thereof, it is possible to prevent mistake from being occurring in selecting the surgical instruments to be used.

Furthermore, it is preferred that each of the surgical instruments as described above is mainly formed of a metallic material such as a stainless steel (SUS316, SUS304, SUS301, or the like), a titanium and a titanium alloy. This makes it possible to provide surgical instruments having high strength so as to be capable of resisting to impact as well as having heat resistance so as to be capable of resisting to heat during sterilization of the instruments.

Figure 16:
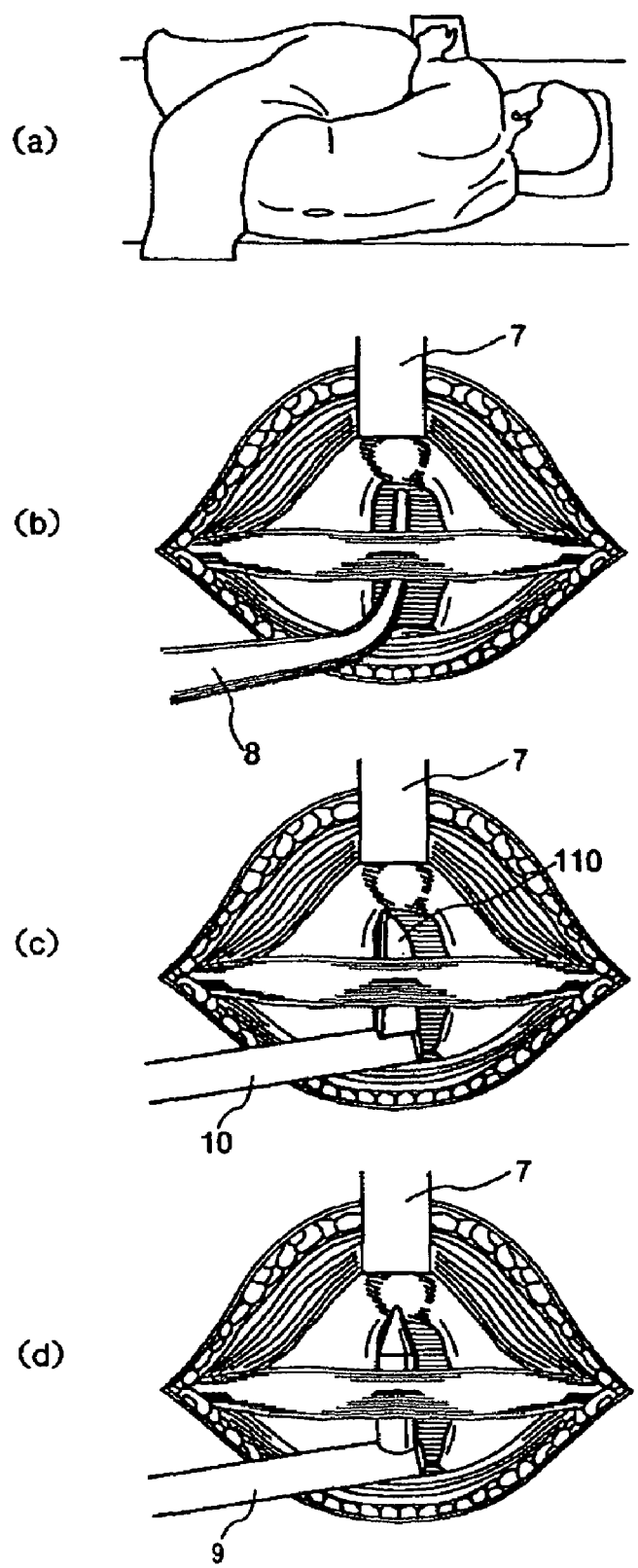
FIG. 16 includes illustrations which explain one example of surgical procedures for inserting the interspinous spacer into a space between adjacent spinous processes using the surgical instruments according to the present invention.
Figure 17:
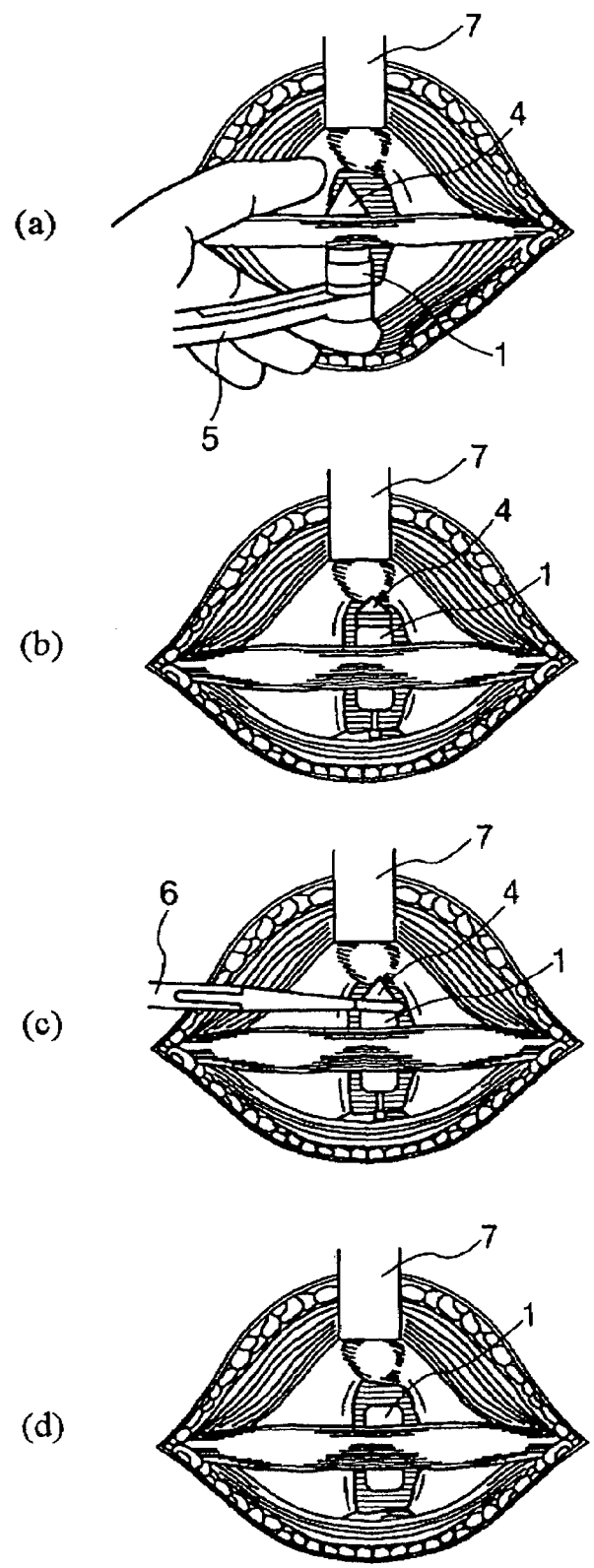
FIG. 17 is continued from FIG. 16 and includes illustrations which explain the surgical procedures for inserting the interspinous spacer into the space between the adjacent spinous processes using the surgical instruments according to the present invention.

Hereinbelow, with reference to FIG. 16 and FIG. 17, an example of a surgical technique for inserting an interspinous spacer 1 into an interspinous space using the surgical instruments according to the present invention will be described.

1 First, as shown in FIG. 16(a), a patient is placed in the flexed right lateral decubitus position, and is locally anesthetized.

2 A skin incision of about 5 cm is made.

3 Muscles are separated from both sides of spinous processes, and are then elevated with a retractor 7.

4 The tip of a curved probe (dilator) 8 is inserted anterior to a supraspinal ligament (see FIG. 16(b)).

5. A distracter 10 is inserted into interspinal ligaments (see FIG. 16(c)). Then, by rotating the insertion part 110 of the distracter 10 to widen the interspinal ligaments. Thereafter, the position of a space between the spinous processes is checked with an X-ray image, and a trial 9 is inserted into the interspinal ligaments to widen the space between the spinous processes (see FIG. 16(d)).

6 As shown in FIG. 11, the insertion instrument 4 which has been inserted into the interspinous spacer 1 is grasped by the grasping instrument 5, and the locking part 521a and the locking part 521b are fitted to each other to lock the condition that the grasping instrument 5 is closed. In this state, the interspinous spacer 1 with the insertion instrument 4 is inserted into a space between the spinous processes from the right side of the patient (see FIG. 17(a)).

7 Then, the locking state of the locking part 521a and the locking part 521b are released to open the grasping instrument 5, and then the grasping instrument 5 is removed (FIG. 17(b)).

8 Then, by using the removal instrument 6, the support part 43 of the insertion instrument 4 is clamed with the clamp portions 63a and 63b of the removal instrument 6 to remove the insertion instrument 4.

9 Then, a fixing member 3 is passed through the hollow portion 22 of the interspinous spacer 1 to fix the spacer 1 between the spinous processes (see FIG. 3).

10 The operative wound is closed.

As described above, the use of the surgical instruments according to the present invention makes it possible to insert an interspinous spacer 1 with a less invasive operation. Further, in particular, by using the insertion instrument 4 as well as the grasping instrument 5, it is possible to push the one end surface of the interspinous spacer 1 with the second abutment portions 531a, 531b when inserting the interspinous spacer 1 into a space between adjacent spinous processes. This means that it is easy to apply a pushing force in an inserting direction of the interspinous spacer 1, and thus the interspinous spacer 1 can be placed easily at a desired position. Further, since it is not necessary to grasp the interspinous spacer 1 with the grasping instrument 5 directly (that is, no grasping force is applied to the interspinous spacer 1 directly), there is no possibility that chipping is caused in the interspinous spacer 1 by excessive grasping force.

In this connection, it is to be noted that one end of the fixing member 3 may be provided near the first end of the insertion instrument 4 (that is, near the end where the grasped portion 42 is provided). With this modification, it is possible to insert the fixing member 3 into the hollow portion 22 of the interspinous spacer 1 by removing the insertion instrument 4 from the interspinous spacer 1, thus enabling to improve the efficiency of the surgical operation further.

Further, it is also to be noted that since the above described operation procedures use the dilator 8 and the trial 9, it is possible to widen the interspinal ligaments easily.

In the foregoing, the surgical instruments according to the present invention were described with reference to the embodiment shown in the drawings, but the present invention is not limited thereto and the structure of each component may be changed to other structure that can exhibit a similar function. For example, the arm members of the grasping instrument and the removal instrument as well as the respective parts or portions thereof (e.g. manipulating portions, grip portions, clamp portions, and the like) may have unsymmetrical configurations.

Further, the surgical instruments according to the present invention are not limited to the embodiment described above, and they may have other instruments or they may be used in combination with other instruments.

Furthermore, the surgical instruments of the present invention may include each of the surgical instruments two or more. For example, the surgical instruments may include the insertion instrument 4 two or more so as to be selectively used to meet the shape and size of an interspinous spacer 1 to be used. Further, the surgical instruments of the present invention may include the grasping instrument 5 and the removal instrument 6 two or more, respectively, so to be selectively used to meet the shape and size of an interspinous spacer 1 to be used.

Furthermore, although in the embodiment described above the arm members 51a, 51b of the grasping instrument 5 are constructed so that the grasping portions 53a, 53b are closed when the manipulating portions 52a, 52b are also closed, a reverse construction may be employed. Namely, the arm members 51a, 51b of the grasping instrument 5 may be constructed so that the grasping portions 53a, 53b are opened when the manipulating portions 52a, 52b are closed.

Further, although in the embodiment described above the arm members 61a, 61b of the removal instrument 6 are constructed so that the clamp portions 63a, 63b are closed when the manipulating portions 62a, 62b are also closed, a reverse construction may be employed. Namely, the arm members 61a, 61b of the removal instrument 6 may be constructed so that the clamp portions 63a, 63b are opened when the manipulating portions 62a, 62b are closed.

Moreover, although in the embodiment described above the surgical instruments include the removal instrument 6, such a removal instrument 6 may be omitted.

Moreover, although in the embodiment described above the first abutment portion 432 of the insertion instrument 4 is formed of a resin material, the present invention is not limited to such a structure. For example, other portions of the insertion instrument 4 which are other than the first abutment portion 432 and adapted to abut on the interspinous spacer 1 may also formed of a resin material. Examples of such portions include the inserting part 41 of the insertion instrument 4 and the grasping portions 53a, 53b of the grasping instrument 5.

Moreover, although in the embodiment described above the insertion instrument 4 has the gradually decreasing part 431, the present invention is not limited thereto and such a gradually decreasing part 431 may be omitted.

Moreover, although in the embodiment described above the grasped portion 42 of the insertion instrument 4 has the first part 421 and the second part 422 having the different cross sections, the present invention is not limited thereto and, for example, the second part 422 may be omitted or a part of the inserting portion 41 may be used as the grasped portion as it is without firming such parts having different cross sections.

Moreover, although in the embodiment described above the interspinous spacer 1 is formed so as to have a substantially cylindrical shape, the present invention is not limited thereto and the interspinous spacer 1 may have any shape such as a substantially spherical shape or a polygonal prismatic shape (e.g., a substantially trigonal prismatic shape, a substantially tetragonal prismatic shape) as long as it includes the hollow portion as described above.

EFFECTS OF THE INVENTION

As described above, according to the present invention, it is possible to insert an interspinous spacer into a space between adjacent spinous processes with easier operations.

Particularly, by using the surgical instruments according to the present invention, it is possible to carry out a less invasive operation without extensive resection of bone or soft tissue.

Finally, it is to be noted that this application is based on Japanese Patent Application No. 2003-149725, the entire disclosure of which is incorporated herein by reference.

What is claimed is:

1. Surgical instruments for use in a surgical operation for inserting an interspinous spacer having a block-like shape formed with a hollow portion into a space between adjacent spinous processes, the surgical instruments comprising:
    an insertion instrument having a first end and a second end opposite to the first end; and
    a grasping instrument to grasp the insertion instrument,
    wherein the insertion instrument having an inserting portion to be passed through the hollow portion of the interspinous spacer, a support portion provided at the second end to prevent the interspinous spacer from falling off from the insertion instrument when the inserting portion is inserted into the hollow portion of the interspinous spacer, and a grasped portion provided near the first end, the grasped portion to be grasped by the grasping instrument in a state that the inserting portion is inserted into the hollow portion of the interspinous spacer so that the interspinous spacer is positioned between the grasped portion and the support portion.

2. The surgical instruments as claimed in claim 1, wherein the support portion has a gradually decreasing part of which cross sectional area gradually decreases toward the second end of the insertion instrument.

3. The surgical instruments as claimed in claim 1, wherein the support portion has a first abutment portion on which one end surface of the interspinous spacer is adapted to abut.

4. The surgical instruments as claimed in claim 1, wherein the grasped portion includes a first part having a cross sectional area in a plane vertical to the longitudinal direction of the insertion instrument, the cross section area of the first part being smaller than that of the insertion portion.

5. The surgical instruments as claimed in claim 4, wherein the grasped portion includes a second part having a cross sectional area larger than that of the first part at the side of the first end from the first part.

6. The surgical instruments as claimed in claim 1, wherein the grasping instrument includes a pair of arm members each having a manipulating portion at the proximal end thereof and a grasping portion at the distal end thereof to grasp the grasped portion, in which the arm members are rotatably coupled at a pivotal point.

7. The surgical instruments as claimed in claim 6, wherein the grasping portions are formed with grooves having a shape corresponding to the shape of the grasped portion to grasp the grasped portion.

8. The surgical instruments as claimed in claim 6, wherein the grasping portions include second abutment portions on which one end surface of the interspinous spacer is adapted to abut.

9. The surgical instruments as claimed in claim 6, wherein the grasping instrument is bent in a direction vertical to the rotational direction of the arm members.

10. The surgical instruments as claimed in claim 8, wherein the grasping instrument is bent toward the side where the second abutment portions are provided.

11. The surgical instruments as claimed in claim 3, wherein the first abutment portions and/or the second abutment portions have surfaces, and at least the surfaces and their vicinities of the first abutment portions and/or the second abutment portions are formed of a resin material.

12. The surgical instruments as claimed in claim 1, wherein the instruments have portions adapted to abut on at least a part of the interspinous spacer, and at least a part of the portions of the instruments is formed of a resin material.

13. The surgical instruments as claimed in claim 11, wherein the resin material is mainly formed of a polyamide resin.

14. The surgical instruments as claimed in claim 1, further including a removal instrument to remove the insertion instrument from the hollow portion of the interspinous spacer.

15. The surgical instruments as claimed in claim 14, wherein the removal instrument includes a pair of arm members each having a manipulating portion at the proximal end thereof and a clamp portion at the distal end thereof to clamp the support portion of the insertion instrument which has been inserted into the hollow portion of the interspinous spacer, in which the arm members are rotatably coupled at a pivotal point.

16. The surgical instruments as claimed in claim 15, wherein each of the clamp portions has a surface, and the surface and its vicinity of each clamp portion is formed of a resin material.

17. The surgical instruments as claimed in claim 16, wherein the resin material is mainly formed of a polyamide resin.

18. The surgical instruments as claimed in claim 15, wherein the clamp portions form a shape corresponding to the shape of the support portion of the insertion instrument.

19. The surgical instruments as claimed in claim 15, wherein the appearance of the manipulating portion of the grasping instrument and the appearance of the manipulating portion of the removal instrument are different from each other.

20. The surgical instruments as claimed in claim 15, wherein each of the instruments can be identified with its manipulating portion.

* * * * *